(12) United States Patent
Juliusson

(10) Patent No.: US 8,088,567 B2
(45) Date of Patent: Jan. 3, 2012

(54) HUMAN IMMORTALISED NEURAL PRECURSOR CELL LINE

(75) Inventor: Bengt Juliusson, Ballerup (DK)

(73) Assignee: NsGene A/S, Ballerup (DK)

( * ) Notice: Subject to any disclaimer, the term of this patent is extended or adjusted under 35 U.S.C. 154(b) by 926 days.

(21) Appl. No.: 11/910,285

(22) PCT Filed: Mar. 30, 2006

(86) PCT No.: PCT/DK2006/000185
§ 371 (c)(1),
(2), (4) Date: Apr. 21, 2008

(87) PCT Pub. No.: WO2006/102902
PCT Pub. Date: Oct. 5, 2006

(65) Prior Publication Data
US 2011/0182983 A1    Jul. 28, 2011

(30) Foreign Application Priority Data

Apr. 1, 2005   (DK) ................................ 2005 00461
Apr. 12, 2005  (DK) ................................ 2005 00523

(51) Int. Cl.
*C12N 15/00* (2006.01)
*C12N 5/00* (2006.01)

(52) U.S. Cl. ........................................ 435/1.1; 435/325

(58) Field of Classification Search .................... None
See application file for complete search history.

(56) References Cited

U.S. PATENT DOCUMENTS

| | | |
|---|---|---|
| 4,844,242 A | 7/1989 | Chen et al. |
| 4,892,538 A | 1/1990 | Aebischer et al. |
| 4,968,733 A | 11/1990 | Müller et al. |
| 4,976,859 A | 12/1990 | Wechs |
| 5,106,627 A | 4/1992 | Aebischer et al. |
| 5,156,844 A | 10/1992 | Aebischer et al. |
| 5,158,881 A | 10/1992 | Aebischer et al. |
| 5,283,187 A | 2/1994 | Aebischer et al. |
| 5,284,761 A | 2/1994 | Aebischer et al. |
| 5,512,600 A | 4/1996 | Mikos et al. |
| 5,550,050 A | 8/1996 | Holland et al. |
| 5,554,148 A | 9/1996 | Aebischer et al. |
| 5,639,275 A | 6/1997 | Baetge et al. |
| 5,653,975 A | 8/1997 | Baetge et al. |
| 5,681,740 A | 10/1997 | Messier et al. |
| 5,773,286 A | 6/1998 | Dionne et al. |
| 5,786,216 A | 7/1998 | Dionne et al. |
| 5,795,790 A | 8/1998 | Schinstine et al. |
| 5,871,487 A | 2/1999 | Warner et al. |
| 5,874,099 A | 2/1999 | Dionne et al. |
| 6,123,700 A | 9/2000 | Mills et al. |
| 6,179,826 B1 | 1/2001 | Aebischer et al. |
| 6,361,771 B1 | 3/2002 | Tao et al. |
| 6,627,422 B1 | 9/2003 | Li et al. |

FOREIGN PATENT DOCUMENTS

| | | |
|---|---|---|
| WO | WO 85/02975 | 7/1985 |
| WO | WO 92/19195 | 11/1992 |
| WO | WO 95/05452 | 2/1995 |
| WO | WO 97/34586 | 9/1997 |
| WO | WO 98/05304 | 2/1998 |
| WO | WO 98/10058 | 3/1998 |
| WO | WO 99/52573 | 10/1999 |
| WO | WO 00/09669 | 2/2000 |
| WO | WO 01/30981 | 5/2001 |
| WO | WO 02/28733 | 4/2002 |
| WO | WO 02/086106 | * 10/2002 |

OTHER PUBLICATIONS

Villa et al, Establishment and properties of a growth factor-dependent, perpetual neural stem cell line from the human CNS. Experimental Neurology [2000, 161(1):67-84].*
"List of Cell Lines", cited in the corresponding European Application No. EP6722877, Publication No. EP1869162, on Oct. 14, 2009.
Andersson et al., "Identification of Intrinsic Determinants of Midbrain Dopamine Neurons," Cell 123: 393-405, 2006.
Buscher et al., "Immunoisolated Xenogenic Chromaffin Cell Therapy for Chronic Pain: Initial Clinical Experience," Anesthesiology 85: 1005-1012, 1996.
Emerich et al., "Alleviation of Behavioral Deficits in Aged Rodents Following Implantation of Encapsulated GDNF-Producing Fibroblasts," Brain Res. 736: 99-110, 1996.
Emerich et al., "Implantation of Polymer-Encapsulated Human Nerve Growth Factor-Secreting Fibroblasts Attenuates the Behavioral and Neuropathological Consequences of Quinolinic Acid Injections into Rodent Striatum," Exp. Neurol. 130: 141-150, 1994.
Emerich et al., "Implants of Polymer-Encapsulated Human NGF-Secreting Cells in the Nonhuman Primate: Rescue and Sprouting of Degenerating Cholinergic Basal Forebrain Neurons," J. Comp. Neurol. 349: 148-164, 1994.
Hoffman et al., "Transplantation of a Polymer-Encapsulated Cell Line Genetically Engineered to Release NGF," Exp. Neurol. 122: 100-106, 1993.
Kordower et al., "Intrastriatal Implants of Polymer Encapsulated Cells Genetically Modified to Secrete Human Nerve Growth Factor: Trophic Effects upon Cholinergic and Noncholinergic Striatal Neurons," Neuroscience 72: 63-77, 1996.
Kordower et al., "The Aged Monkey Basal Forebrain: Rescue and Sprouting of Axotomized Basal Forebrain Neurons after Grafts of Encapsulated Cells Secreting Human Nerve Growth Factor," Proc. Natl. Acad. Sci. USA 91: 10898-10902, 1994.

(Continued)

*Primary Examiner* — Sheridan Swope
(74) *Attorney, Agent, or Firm* — Kristina Bieker-Brady; Clark & Elbing LLP

(57) ABSTRACT

The present invention relates to an immortalized human neural precursor cell line, NGC-407. The cell line has been established from human foetal tissue. The cell line has been immortalized using a retroviral vector containing the v-myc oncogene. The cell line is a neural progenitor cell line capable of differentiating into to astrocytes and neurons including dopaminergic neurons. NGC-407 cells are capable of migrating to glioblastoma tumours implanted into rat brains and form gap junctions with the tumour cells. NGC-407 cells expressing a suicide gene can be be used for delivering activated prodrugs in the form of activated nucleoside analogs to tumours.

26 Claims, 4 Drawing Sheets

OTHER PUBLICATIONS

Li et al., "Bystander Effect-Mediated Gene Therapy of Gliomas Using Genetically Engineered Neural Stem Cells," Cancer Gene Ther. 12: 600-607, 2005.

Lindner et al., "Effects of Intraventricular Encapsulated hNGF-Secreting Fibroblasts in Aged Rats," Cell Transplant. 5: 205-223, 1996.

Lotharius et al., "Effect of Mutant a-Synuclein on Dopamine Homeostasis in a New Human Mesencephalic Cell Line," J. Biol. Chem. 277: 38884-38894, 2002.

Martinez-Serrano et al., "Human Neural Stem and Progenitor Cells: In Vitro and in Vivo Properties, and Potential for Gene Therapy and Cell Replacement in the CNS," Curr. Gene Ther. 1: 279-299, 2001.

Miljan et al., "Characterization of ReNcell VM: A Human Dopaminergic Cell Line," Poster presented at ISSCR Annual Meeting, 2004.

Villa et al., "Establishment and Properties of a Growth Factor-Dependent Perpetual Neural Stem Cell Line from the Human CNS," Exp. Neurol. 161: 67-84, 2000.

Winn et al., "Polymer-Encapsulated Cells Genetically Modified to Secrete Human Nerve Growth Factor Promote the Survival of Axotomized Septal Cholinergic Neurons," Proc. Natl. Acad. Sci. USA 91: 2324-2328, 1994.

* cited by examiner

NGC-407

NGC-407, ZG561

HUMAN IMMORTALISED NEURAL PRECURSOR CELL LINE

The present invention relates to an immortalised human neural precursor cell line, NGC-407. The cell line has been established from human foetal tissue.

BACKGROUND

The efficacy of treating neurodegerative disorders with transplantation of human fetal tissue has been shown in animal models [Brundin, et al, Behavioural effects of human fetal dopamine neurons grafted in a rat model of Parkinson's disease, *Exp Brain Res,* 65 (1986) 235-40.; Wictorin et al, Reformation of long axon pathways in adult rat central nervous system by human forebrain neuroblasts, *Nature,* 347 (1990) 556-8.] as well as in patients with Parkinson's disease (PD) and Huntington's disease [Bachoud-Levi et al, Motor and cognitive improvements in patients with Huntington's disease after neural transplantation, *Lancet,* 356 (2000) 1975-9.; Freed et al, Transplantation of embryonic dopamine neurons for severe Parkinson's disease, *N Engl J Med,* 344 (2001) 710-9.; Hagell et al, Sequential bilateral transplantation in Parkinson's disease: effects of the second graft, *Brain,* 122 (Pt 6) (1999) 1121-32.; Kordower et al, Neuropathological evidence of graft survival and striatal reinnervation after the transplantation of fetal mesencephalic tissue in a patient with Parkinson's disease, *N Engl J Med,* 332 (1995) 1118-24.; Lindvall et al, Grafts of fetal dopamine neurons survive and improve motor function in Parkinson's disease, *Science,* 247 (1990) 574-7; Olanow et al, Fetal nigral transplantation as a therapy for Parkinson's disease, *Trends Neurosci,* 19 (1996) 102-9.]. However, human-derived fetal donor cells gives rise to both ethical and practical dilemmas, and therefore, alternative cell sources for future transplantations have to be developed. Implantation of cells genetically modified to express therapeutic genes into the brain has been proposed as a potential treatment for neurodegenerative disorders [Villa, A., Navarro, B. and Martinez-Serrano, A., Genetic perpetuation of in vitro expanded human neural stem cells: cellular properties and therapeutic potential, *Brain Res Bull,* 57 (2002) 789-94.]. Thus, when combining genetic engineering and cell transplantation, an important issue is to find a suitable cell vehicle.

Tumour cells modified to express a Thymidine Kinase (TK) gene acquire the ability to convert the non-toxic nucleoside analog ganciclovir (GCV) to its cytotoxic metabolite ganciclovir-triphosphate. Cells genetically engineered to express this "suicide" gene are eliminated if exposed to ganciclovir. Experimental tissue culture of tumour cells as well as brain tumour implants, consisting of a mixture of TK-expressing cells and unmodified "native" tumour cells also regress following ganciclovir treatment without harm to adjacent normal tissue. This phenomenon, where a minority of TK-expressing cells lead to the death and elimination of adjacent native tumour cells not expressing TK, has been termed the "bystander effect".

Malignant brain tumours are an appealing target for suicide gene delivery, since the entire malignancy is confined to the brain and amenable to eradication by the bystander effect. Key components for the success of this strategy are the genetic vector from which the suicide gene is expressed and its delivery vehicle. As it is impossible to target all individual tumours in e.g. glioblastoma multiforme with separate injections of a gene therapy vector another delivery strategy is needed. Migrating cells that are capable of tracking down glioma cells and that have been engineered to deliver a therapeutic molecule represent an ideal solution to the problem of glioma cells invading normal brain tissue. It has been demonstrated that the migratory capacity of neural stem cells (NSCs) is ideally suited to therapy in neurodegenerative disease models that require brain-wide cell replacement and gene expression. It has been hypothesized that NSCs may specifically home to sites of disease within the brain. Studies have also yielded the intriguing observation that transplanted NSCs are able to home into a primary tumour mass when injected at a distance from the tumour itself; furthermore, NSCs were observed to distribute themselves throughout the tumour bed, even migrating in juxtaposition to advancing single tumour cells (Dunn & Black, Neurosurgery 2003, 52:1411-1424; Aboody et al, PNAS, 2000, 97:12846-12851). These authors showed that NSCs were capable of tracking infiltrating glioma cells in the brain tissue peripheral to the tumour mass, and "piggy back" single tumour cells to make cell-to-cell-contact.

The present invention addresses several problems in the area of treatment of neurodegenerative disorders and in the treatment of cancer It is thus one object of the invention to provide sufficient material for replacement cell therapy obviating the need for large amounts of foetal tissue. It is another object to provide cells capable of stably expressing transgenes after transplantation into the CNS. It is a further object to provide cells capable of forming gap junctions with cancer cells. It is also an object to provide cells capable of tracing cancer cells in the CNS. Finally, such cells should be able to proliferated such that they can be passaged enough to be expanded, transfected with therapeutic genes and banked.

SUMMARY OF THE INVENTION

The present invention in one aspect relates to a human cell line obtainable from or derived from or constituted by NGC-407 cells. The cell line has been deposited under the Budapest Treaty with Deutsche Sammlung von Mikroorganismen and Zellkulturen GmbH, Mascheroder Weg 1b, D-38124 Braunschweig, Germany on the 31 of Mar., 2005 under accession number DSM ACC2718.

The cell line of the invention has several advantages. It is a stable, immortalised cell line which has been expanded and has remained stable during more than 130 population doublings. The cell line is a neural progenitor cell line, which can differentiate into neurons, astrocytes and dopaminergic neurons depending on the differentiation conditions. The NGC-407 cell line can be used for transplantation. It has been shown that the cell line can survive transplantation for at least 3 weeks in rats. It is therefore expected that the NGC-407 cell line can survive for an even longer time in human brains. During the transplantation period, the cell line can stably express a heterologous gene. The NGC-407 cell line therefore can be used both for replacement therapy (replacement of lost or damaged cells of the nervous system) and for protective therapy (as a vehicle to deliver a biological function such as a secreted growth factor, neurotrophic factor or neurotransmitter).

The cell line has also been transduced to express a heterologous thymidine kinase. Monoclonal cell lines expressing high levels of this heterologous kinase have been selected.

These cell lines can be used as vehicles for delivery of thymidine kinase to tumour cells in the nervous system. It has also been shown that the NGC-407 cell line can migrate towards cancer cells in the central nervous system, and that the NGC-407 cell line can form gap junctions with cancer cells and transfer low molecular weight compounds from the cell line to the cancer cells. The NGC-407 cell line can therefore be used as a delivery vehicle to activate prodrugs (e.g. AZT, ganciclovir) after the cell line has migrated to cancer cells and formed gap junctions with these. The activated prodrugs will then be transferred to the cancer cells and kill both these and the delivery cell line. This is a feasible and promising way of treating glioblastoma multiforme.

In a further aspect, the invention relates to use of the NGC-407 cell line for experimental purposes such as in vitro drug screening and characterisation. This could e.g. be part of a safety and toxicity study. Compared to a known cell line of mesencephalic origin (MES-II(1)-C2, described in WO 00/09669; also known as MESC2.10 described in Lotharius et al J Biol Chem 2002, 277:38884-38894) NGC-407 expresses the stem cell marker, Nestin, and is capable of differentiating into both neurons and astrocytes. MESC2.10 on the other hand does not express nestin and can only be induced to differentiate into neurons. NGC-407 thus represents an earlier developmental stage and has a broader potential compared to MESC2.10. Astrocytes secrete a number of growth factors (including GDNF) and hormones that are of importance for maintaining the functionality of neurons. In terms of identification of potential biologics drugs for treatment of e.g. Parkinson's Disease, a cell line containing a significant proportion of astrocytes therefore represents a better model system compared to a neuronal cell line.

In another aspect, the invention relates to use of the NGC-407 cell line for therapeutic applications and in a further aspect for replacement therapy. In a particularly preferred embodiment, the cell line is used for cancer therapy.

In a further aspect, the invention relates to a biocompatible capsule comprising a core comprising a composition of cells derived from NGC-407 cell line, said cells being capable of secreting a compound delivering a biological function to an individual; and semi-permeable membrane surrounding the composition of cells and allowing the passage of a compound secreted by the composition of cells.

In one embodiment of the present invention, "treatment", "therapy", and "medical use" is intended to cover prophylaxis. "Treatment", "therapy" and "medical use" may also cover inhibition of a disease or disorder, protection against a disease or disorder, and/or prevention (not absolute) of a disease or disorder. "Treatment", "therapy" and "medical use" may also comprise curative, ameliorative, and/or symptomatic treatment, therapy and medical use.

BRIEF DESCRIPTION OF THE DRAWINGS

In FIG. 1A TH labelled neurons are marked with arrows. In FIG. 1B β-III-tubulin labelled cells are marked with arrows and GFAP labelled cells are marked with arrowheads.

DETAILED DESCRIPTION

Figure 1:
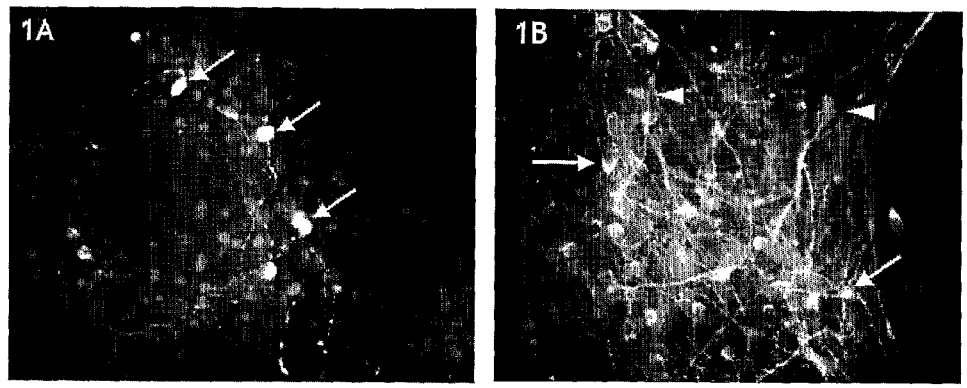
FIG. 1 shows photographs of differentiated immunolabelled NGC-407 cells.

Transfection or Transduction of NGC-407 Cell Line

In a preferred embodiment, cells derived from the NGC-407 cell line of the invention comprise, integrated into the genome and replicated together with the chromosome(s) into which it has been integrated, the heterologous DNA elements, in operable combination, of a eukaryotic promoter, a heterologous therapeutic gene, a polyadenylation signal (pA).

The heterologous DNA elements may be of any suitable origin, but preferably selected among those described herein.

In a preferred embodiment, the heterologous therapeutic gene may be expressed under the transcriptional control of the human ubiquitin (UbC) promoter.

A possible down-regulation of expression may be circumvented by procedures that direct a site specific integration of the transgene and its accompanying promoter.

According to one embodiment of the invention, the promoter is a constitutive promoter selected from the group consisting of: ubiquitin promoter, CMV promoter, JeT promoter (US 6,555,674), SV40 promoter, Elongation Factor 1 alpha promoter (EF1-alpha), RSV, and Mo-MLV-LTR.

Examples of inducible/repressible promoters include: Tet-On, Tet-Off, Rapamycin-inducible promoter, Mx1.

Suitable expression control sequences include promoters, enhancers, transcription terminators, start codons, splicing signals for introns, and stop codons, all maintained in the correct reading frame of the polynucleotide of the invention so as to permit proper translation of mRNA. Expression control sequences may also include additional components such as leader sequences and fusion partner sequences.

Suitable expression vectors may be a viral vector derived from *Herpes simplex*, alphavirus, adenovirus, adeno associated virus, baculovirus, HSV, coronavirus, Bovine papilloma virus, Mo-MLV, preferably adeno associated virus, or from various bacterially produced plasmids.

Other transfection methods include, but are not limited to, liposome transfection, electroporation, and transfection with carrier peptides containing nuclear or other localising signals.

Other suitable expression vectors include general purpose mammalian vectors which are also obtained from commercial sources (Invitrogen Inc., Clontech, Promega, BD Biosecences, etc) and contain selection for Geneticin/neomycin (G418), hygromycin B, puromycin, Zeocin/bleomycin, blasticidin SI, mycophenolic acid or histidinol.

The vectors include the following classes of vectors: general eukaryotic expression vectors, vectors for stable and transient expression and epitag vectors as well as their TOPO derivatives for fast cloning of desired inserts (see list below for non-limiting examples of vectors).

Ecdysone-Inducible Expression: pIND(SP1) Vector; pINDN5-His Tag Vector Set; pIND(SP1)/V5-His Tag Vector Set; EcR Cell Lines; Muristerone A.

Stable Expression: pcDNA3.1/Hygro; PCI; PSI; pSecTag A, B & C; pcDNA3.1(−)/MycHis A, B & C; pcDNA3.1 +/−; pcDNA3.1/Zeo (+) and pcDNA3.1/Zeo (−); pcDNA3.1/His A, B, & C; pRc/CMV2; pZeoSV2 (+) and pZeoSV2 (−); pRc/RSV; pTracer™-CMV; pTracer™-SV40.

Transient Expression: pCDM8; pcDNA1.1; pcDNA1.1/Amp.

Epitag Vectors: pcDNA3.1/MycHis A, B & C; pcDNA3.1N5-His A, B, & C.

Heterologous Therapeutic Genes

The heterologous therapeutic gene is a gene encoding a therapeutically active polypeptide or proteins (also designated a therapeutic factor). Preferred therapeutically active polypeptides or proteins are polypeptides or proteins that are capable of ameliorating or treating neurological disorders.

In a preferred embodiment, the heterologous therapeutic gene is encoding a neurotrophic factor. In a more preferred embodiment, the neurotrophic factor is a Nerve Growth Factor (NGF); an Insulin-like Growth Factor (IGF), in particular IGF I or IGF II; a member of the Transforming Growth Factor (TGF) superfamily, including a Transforming Growth Factor-α and -β (TGFα and TGFβ), Transforming Growth Factor-β2 (TGF-β2), Neurturin (NTN), Persephin (PSP); a Glial cell-line Derived Neurotrophic Factor (GDNF); Neublastin (NBN); a Ciliary Neurotrophic Factor (CNTF); a Brain Derived Neurotrophic Factor (BDNF); a Neurotrophin (NT), in particular NT 3 to 9; a Tumor Necrosis Factor (TNF), in particular TNF-α.

In another preferred embodiment, the heterologous therapeutic gene is encoding a neuronal survival factor. In a more preferred embodiment, the neuronal survival factor is a soluble or secreted Super Oxide Dismutase (SOD), Bcl2, BclX$_L$, or a Hedgehog protein.

In a third preferred embodiment, the heterologous therapeutic gene is encoding a nerve growth factor. In a more preferred embodiment, the nerve growth factor is a Fibroblast Growth Factor (FGF), in particular an acidic or a basic Fibroblast Growth Factor (aFGF or bFGF); an Endothelial Growth Factor (EGF), in particular a Vascular Endothelial Growth and Permeability Factor (VEGPF); an interferon, in particular Interferon-α, Interferon-β or Interferon-γ; an interleukin (IL), in particular IL-1, IL-1β, GMCSF, and IL 2 to 14.

In a fourth preferred embodiment, the heterologous therapeutic gene is encoding a biologically active molecule that participates in the synthesis of a neurotransmitter substance. In a more preferred embodiment, the neurotransmitter substance is acetylcholine, noradrenaline, adrenaline, 3,4-dihydroxyphenylalanine (L-DOPA), dopamine, octopamine, glutamate, aspartate, glycine, proline, χ-aminobutyric acid (GABA), tyrosine, taurine, alanine, cystathione, histamine, serotonine(5-hydroxytryptamine), substance P, Neuropeptid Y (NPY), Cholecystokinin, neurotensin, enkephalins, or somatostatin. In another preferred embodiment, the biologically active molecule that functions in the synthesis of a neurotransmitter substance is a choline acetyl transferase; a Tyrosine Hydroxylase (TH); a tyrosine decarboxylase; a thymidine kinase, a cytosine deamidase, a monoamine oxidase, a L-DOPA decarboxylase, a histidine decarboxylase, a glutamate decarboxylase, an Ornithine Transcarbamylase (OTC).

In a fifth preferred embodiment, the heterologous therapeutic gene is encoding a receptor. In a more preferred embodiment, the receptor is a receptor which binds acetylcholine, noradrenaline, adrenaline, 3,4-dihydroxyphenylalanine (L-DOPA), dopamine, octopamine, glutamate, aspartate, glycine, proline, χ-aminobutyric acid (GABA), tyrosine, taurine, alanine, cystathione, histamine, serotonine (5-hydroxytryptamine), substance P, Neuropeptid Y (NPY), Cholecystokinin, neurotensin, enkephalins, or somatostatin.

Replacement Therapy

The cell lines of, the invention may or may not be manipulated so as to contain additional heterologous DNA encoding specific therapeutic factors. In case the cell line of the invention does not contain additional heterologous DNA encoding specific therapeutic factors it may be particularly suited for restorative therapy.

As defined herein, replacement therapy relates to the transplantation of cells of origin in the nervous system which, after engraftment, replace defective, absent or lost cells and their functions, at specific locations, or globally in the CNS and/or PNS.

In a further aspect the invention provide provides methods and compositions for use in replacement therapy within the CNS or outside the CNS. Replacement therapy of the invention may in particular be applied to cell replacement, delivery of cell-secreted endogenous substance produced by the cells, therapy for the hematopoeitic system, neurological diseases in mammals, including humans.

The neurological deficits contemplated according to the invention include any neuro-degenerative disease, disorder or condition. The neurological deficit may in particular be a neurodegenerative disease involving lesioned and traumatic neurons, in particular traumatic lesions of peripheral nerves, the medulla, and/or the spinal cord, cerebral ischaemic neuronal damage, neuropathy and especially peripheral neuropathy, Alzheimer's disease, Huntington's disease, Parkinson's disease, glioblastoma, amyotrophic lateral sclerosis or any other neurodegenerative disease, and memory impairment connected to dementia.

Protective Therapy

While an immortalised cell line of the invention not holding additional heterologous DNA encoding specific therapeutic factors may be particularly well suited for replacement therapy, the immortalised cell line of the invention that has been subjected to the introduction of additional heterologous DNA encoding specific therapeutic factors may be particular well suited for protective therapy.

As defined herein, protective therapy relates to the transplantation of cells of origin in the nervous system which, after engraftment, produce either endogenous or exogenous therapeutic factors that will prevent, or protect cell death or dysfunction in the nervous system of the recipient individual, or stimulate function or regenerative and re-innervation capacity of these cells, at specific locations or globally in the CNS and/or PNS.

In particular the invention provides methods and compositions for use in protective therapy. More specifically the invention provides methods and compositions for use by implantation with therapeutic and/or preventive intent into the brains of normal or immune-suppressed mammals, including humans. In particular the invention provides methods and compositions useful for sustainable and safe remediation of neurological deficits.

The neurological deficits contemplated according to the invention include any neuro-degenerative disease, disorder or condition. The neurological deficit may in particular be a neurodegenerative disease involving lesioned and traumatic neurons, in particular traumatic lesions of peripheral nerves, the medulla, and/or the spinal cord, cerebral ischaemic neuronal damage, neuropathy and especially peripheral neuropathy, Alzheimer's disease, Huntington's disease, Parkinson's disease, glioblastoma, amyotrophic lateral sclerosis or any other neurodegenerative disease, and memory impairment connected to dementia.

Differentiation

The NGC-407 cell line may be subjected to known differentiation treatments in vitro such as those described in Example 1 (Bardford differentiation; Sah differentiation; Storch differentiation) in addition to other known differentiation methods such as the TH induction method described in WO 02/086106 (NsGene). Such differentiation may be performed prior to replacement therapy or as part of an in vitro assay or gene expression profiling.

A further illustrative example of differentiation protocols include the two protocols described in Example 8 (differentiation in N2 medium without EGF and bFGF (N2 differentiation); differentiation in N2 medium without EGF and bFGF and with cAMP and GDNF (DA differentiation medium)).

Furthermore, NGC-407 cells may be differentiated by transducing or transfecting with an expression vector coding for transcription factors responsible for or involved in dopaminergic differentiation such as Nurr1, Pitx3, En and Lmx1b. A preferred transcription factor is Lmx1a as described by Andersson et at (Andersson et at 2006, "Identification of intrinsic determinants of midbrain dopamine neurons", Cell 124: 393-405).

In Vitro Assays

The NGC-407 cell line can be used to test potential drugs (both low molecular weight and proteins, genes or IRNA) in various in vitro assays. Briefly, the cell line is exposed to a compound of interest and the response is compared to a control treatment. The response may be survival, differentiation, metabolic activity, signalling, receptor activation etc.

Gene Profiling

The NGC-407 cell line has been established from human foetal ventral midbrain at approximately the time when the ventral midbrain develops dopaminergic neurons. Genes, the regulation of which is specific to NGC-407, may thus be used as markers of cells from the ventral midbrain, as markers of dopaminergic neurons, or as markers of stem cells/progenitor cells from the ventral midbrain. Genes identified using NGC-407 may also be tested for therapeutic potential.

Suicide Gene Therapy

As described in the Background part of the present application, neural stem cells can be used as a delivery vehicle to deliver the product of a suicide gene to cancer cells. As evidenced by the examples herein NGC-407 is indeed capable of migrating to gliobastoma tumours while maintaining expression of a marker gene (GFP). The cell line may therefore be used as a vehicle to deliver a heterologous suicide gene to tumours. It has been observed that administration of 4-PB increases the number of GFP positive cells around the implanted tumours. Thus in a preferred embodiment, 4-PB is administered to a patient to whom suicide gene expressing NGC-407 cells have been implanted. Methods and dosages for administration of 4-PB and analogs in connection with suicide gene therapy are described in WO 2005/079849.

Deoxyribonucleoside Kinases

In a preferred embodiment of bystander mediated suicide gene therapy, the cell line of the invention has been genetically engineered to overexpress a heterologous deoxyribonucleoside kinase. Deoxyribonucleoside kinases (dNK) from various organisms differ in their substrate specificity, regulation of gene expression and cellular localisation. In mammalian cells there are four enzymes with overlapping specificities, the thymidine kinases 1 (TK1) and 2 (TK2), deoxycytidine kinase (dCK) and deoxyguanosine kinase (dGK) phosphorylate purine and pyrimidine deoxyribonucleosides. TK1 and TK2 are pyrimidine specific and phosphorylate deoxyuridine (dUrd) and thymidine (dThd), and TK2 also phosphorylates deoxycytidine (dCyd). dCK phosphorylates dCyd, deoxyadenosine (dAdo) and deoxyguanosine (dGuo), but not dThd. dGK phosphorylates dGuo and dAdo. In mammals, TK1 is cytosolic, and TK2 and dGK are localised in the mitochondria, although recent reports indicate a cytoplasmic localisation of TK2 as well.

The best known and most studied example of suicide gene therapy is Herpes simplex virus (HSV) thymidine kinase (tk) gene (Karreman, 1998, A new set of positive/negative selectable markers for mammalian cells. Gene. 218: 57-61). The HSV tk gene leads to cell death when growing cells are exposed to antiherpetic nucleoside analogs such as ganciclovir (GCV), as this and other prodrugs are metabolised by HSV TK to toxic metabolites.

A *Drosophila melanogaster* deoxyribonucleoside kinase (Dm-dNK) phosphorylates all four natural deoxyribonucleosides as well as several nucleoside analogs (Munch-Petersen et al., 1998, Four deoxynucleoside kinase activities from Drosophila melanogaster are contained within a single monomeric enzyme, a new multifunctional deoxynucleoside kinase. J Biol Chem. 273: 3926-31; Munch-Petersen et al 2000, Functional expression of a multisubstrate deoxyribonucleoside kinase from Drosophila melanogaster and its C-terminal deletion mutants. J Biol Chem. 275: 6673-9; WO 00/36099 "New medical use of gene and vector encoding a multisubstrate deoxyribonucleoside kinase (dNK)"). The broad substrate specificity of this enzyme together with a high catalytic rate makes it unique among the nucleoside kinases for use as a suicide gene in combined gene/chemotherapy of cancer.

Mutant forms of the *Drosophila melanogaster* Dm dNK have been developed, which have broad substrate specificities (WO 01/88106 "Multi-substrate insect deoxynucleoside kinase variants"). A particularly preferred variant is the variant B5 because its degree of activation is approximately 50 times better than wild type Dm dNK for gemcitabine. The degree of activation is defined as the ratio of the $IC_{50}$ of the prodrug in the nontransfected cell line to the $IC_{50}$ of the nucleoside analogue in the transfected cell line.

These and other recombinant kinases in a gene therapy approach can be overexpressed in NGC-407 cells by placing them under the control of a strong constitutive promoter, such as the CMV promoter, human UbiC promoter, JeT promoter (U.S. Pat. No. 6,555,674), SV40 promoter, and Elongation Factor 1 alpha promoter (EF1-alpha).

Non-limiting examples of specific known sequences of deoxyribonucleoside kinases comprise for example the following:

HSV-tk wild type ACCESSION V00470
(SEQ ID NO 1)
MASYPGHQHASAFDQAARSRGHSNRRTALRPRRQQEATEVRPQKMPTLLRVYIDGPHGMGKTTTTQLLVA

LGSRDDIVYVPEPMTYWRVLGASETIANIYTTQHRLDQGEISAGDAAVVMTSAQITMGMPYAVTDAVLAP

HIGGEAGSSHAPPPALTLIFDRHPIAALLCYPAARYLMGSMTPQAVLAFVALIPPTLPGTNIVLGALPED

RHIDRLAKRQRPGERLDLAMLAAIRRVYGLLANTVRYLQCGGSWREDWGQLSGTAVPPQGAEPQSNAGPR

PHIGDTLFTLFRAPELLAPNGDLYNVFAWALDVLAKRLRSMHVFILDYDQSPAGCRDALLQLTSGMVQTH

VTTPGSIPTICDLARTFAREMGEAN

*Drosophila melanogaster* wildtype kinase GenBanK ACCN Y18048
(SEQ ID NO 2)
MAEAASCARKGTKYAEGTQPFTVLIEGNIGSGKTTYLNHFEKYKNDICLLTEPVEKWRNVNGVNLLELMY

KDPKKWAMPFQSYVTLTMLQSHTAPTNKKLKIMERSIFSARYCFVENMRRNGSLEQGMYNTLEEWYKFIE

ESIHVQADLIIYLRTSPEVAYERIRQRARSEESCVPLKYLQELHELHEDWLIHQRRPQSCKVLVLDADLN

LENIGTEYQRSESSIFDAISSNQQPSPVLVSPSKRQRVAR

Tomato TK
(SEQ ID NO 3)
MAFSSSARNPVDLRNGSKNSFCPVGEIHVIVGPMFAGKTTALLRRVNLESNDGRNVVLIKSSKDARYAVD

AVVTHDGTRFPCWSLPDLSSFKQRFGKDAYEKVDVIGIDEAQFFGDLYEFCCNAADFDGKIIVVAGLDGD

YLRKSFGSVLDIIPLADTVTKLTARCELCNRRAFFTFRKTNETETELIGGADIYMPVCRQHYVNGQSVNE

SAKMVLESHKVSNELILESPLVDP

*Arabidopsis thaliana* dNK
(SEQ ID NO 4)
MVDYLRSSVGIIHRNHAESITTFIKESVDDELKDSGPEPNLNVKKRLTFCVEGNISVGKSTFLQRIANET

VELQDLVEIVPEPVDKWQDVGPDHFNILDAFYSEPQRYAYTFQNYVFVTRLMQEKESASGVKPLRLMERS

VFSDRMVFVRAVHEAKWMNEMEISIYDSWFDPVVSSLPGLVPDGFIYLRASPDTCHKRMMLRKRAEEGGV

SLKYLQDLHEKHESWLLPFESGNHGVLSVSRPSLHMDNSLHPDIKDRVFYLEGNHMHSSIQKVPALVLDC

EPNIDFSRDIEAKTQYARQVAEFFEFVKKKQETSTEKSNSQSPVLLPHQNGGLWMGPAGNHVPGLDLPPL

DLKSLLTRPSA

*Drosophila melanogaster*, mutant 85
(SEQ ID NO 5)
MAEAASCARKGTKYAEGTQPFTVLIEGNIGSGKTTYLNHFEKYKNDICLLTEPVEKWRNVNGVNLLELMY

KDPKKWAMPFQSYATLTMLQSHTAPTNKKLKIMERSIFSARYCFVENMRRNGSLEQGMYNTLEEWYKFIE

ESIHVQADLIIYLRTSPEVAYERIRQRARSEESCVPLKYLQELHELHEDWLIHQRRPQSCKVLVLDADLD

LENIGTEYQRSESSIFDAISSNQQPSPVPVSPSKRQRVAR

*Arabidopsis thaliana* dCGK NP_565032
(SEQ ID NO 6)
```
  1 mqkilckstt sstpvlstpv nslaagfisl gfktpvknlp pcsttkplst cffstsampt
 61 ttasvssggv gfsaylqrtv hkpapasvrf stagyrtcrc sidgtnrawv grtgswralf
121 csdstggltp vnatagavve seeesdgede deekdekpvr mnrrnrsssg sgefvgnpdl
181 lkipgvglrn qrklvdngig dvaelkklyk dkfwkasqkm vdylrssvgi ihrnhaesit
241 tfikesvdde lkdsgpepnl nvkkrltfcv egnisvgkst flqrianetv elqdlveivp
301 epvdkwqdvg pdhfnildaf ysepqryayt fqnyvfvtrl mqekesasgv kplrlmersv
361 fsdrmvfvra vheakwmnem eisiydswfd pvvsslpglv pdgfiylras pdtchkrmml
421 rkraeeggvs lkylqdlhek heswllpfes gnhgvlsvsr pslhmdnslh pdikdrvfyl
```

-continued 481 egnhmhssiq kvpalvldce pnidfsrdie aktqyarqva effefvkkkq etsteksnsq 541 spvllphqng glwmgpagnh vpgldlppld ksllltrpsa

*Oryza sativa* dCGK BAB86213
(SEQ ID NO 7)
  1 mveflqssvg iihknhaesi tlfikesvde elkgtdspnv sknkrltfcv egnisvgktt 61 flqrianeti elrdlveivp epiakwqdvg pdhfnildaf yaepqryayt fqnyvfvtrv 121 mqekesssgi kplrlmersv fsdrmvvkfl kvfvravhea nwmnemeisi ydswfdpvvs 181 slpglipdgf iylraspdtc hkrmmvrkrs eeggvtldyl rglhekhesw llpskgqgpg 241 vlsvsqvpvh megslppdir ervfylegdh mhssiqkvpa lvldcehdid fnkdieakrq

*H. sapiens* dCK XP_003471
(SEQ ID NO 8)
MATPPKRSCPSFSASSEGTRIKKISIEGNIAAGKSTFVNILKQLCEDWEVVPEPVARWCNVQSTQDEFEE

LTMSQKNGGNVLQMMYEKPERWSFTFQTYACLSRIRAQLASLNGKLKDAEKPVLFFERSVYSDRYIFASN

LYESECMNETEWTIYQDWHDWMNNQFGQSLELDGIIYLQATPETCLHRIYLRGRNEEQGIPLEYLEKLHY

KHESWLLHRTLKTNFDYLQEVPILTLDVNEDFKDKYESLVEKVKEFLSTL

*H. sapiens* dGK XP_002341
(SEQ ID NO 9)
MAAGRLFLSRLRAPFSSMAKSPLEGVSSSRGLHAGRGPRRLSIEGNIAVGKSTFVKLLTKTYPEWHVATE

PVATWQNIQAAGNQKACTAQSLGNLLDMMYREPARWSYTFQTFSPLSRLKVQLEPFPEKLLQARKPVQIF

ERSVYSDRYIFAKNLFENGSLSDIEWHIYQDWHSFLLWEFASRITLHGFIYLQASPQVCLKRLYQRAREE

EKGIELAYLEQLHGQHEAWLIHKTTKLHFEALMNIPVLVLDVNDDFSEEVTKQEDLMREVNTFVKNL

*H. sapiens* TK2 NP_004605
(SEQ ID NO 10)
MGAFCQRPSSDKEQEKEKKSVICVEGNIAGGKTTCLEFFSNATDVEVLTEPVSKWRNVRGHNPLGLMYH

DASRWGLTLQTYVQLTMLDRHTRPQVSSVRLMERSIHSARYIFVENLYRSGKMPEVDYVVLSEWFDWIL

RNMDVSVDLIVYLRTNPETCYQRLKKRCREEEKVIPLEYLEAIHHLHEEWLIKGSLFPMAAPVLVIEAD

HHMERMLELFEQNRDRILTPENRKHCP

*H. sapiens* TK1 XP_037195
(SEQ ID NO 11)
MSCINLPTVLPGSPSKTRGQIQVILGPMFSGKSTELMRRVRRFQIAQYKCLVIKYAKDTRYSSSFCTHD

RNTMEALPACLLRDVAQEALGVAVIGIDEGQFFPDIMEFCEAMANAGKTVIVAALDGTFQRKPFGAILN

LVPLAESVVKLTAVCMECFREAAYTKRLGTEKEVEVIGGADKYHSVCRLCYFKKASGQPAGPDNKENCP

VPGKPGEAVAARKLFAPQQILQCSPAN

*Bombyx mori* dNK AAK28318
(SEQ ID NO 12)
  1 msannvkpft vfvegnigsg kttflehfrq feditlltep vemwrdlkgc nllelmykdp 61 ekwamtfqsy vsltmldmhr rpaptpvklm erslfsaryc fvehimrnnt lhpaqfavld 121 ewfrfiqhni pidadlivyl ktspsivyqr ikkrarseeq cvplsyieel hrlhedwlin 181 rihaecpapv lvldadldls qitdeykrse hqilrkavnv vmsspnkhsp kkpisttpik 241 itphmril

*Anopheles* dNK AAO49462
(SEQ ID NO 13)
MPPIASEKLGASGKKPFTVFVEGNIGSGKTTFLNHFQKFNDICLLTEPVEKWRNCGGVNL

LDLMYKESHRWAMPFQTYVTLTMLDMHTCQTDKSVKLMERSLFSARNCFVESMLASGSLH

QGMYNVLQEWYDFICCNIHIQADLIVYLQTSPEVVYERMKQRARSEESCVPLEYLKELHE

LHENWLIHGASPRPAPVLVLNADLDLNTIGAEYERSETSILKPILIENTNQHAILTSPAK

RAKTDF

Rice TK1

(SEQ ID NO 14)
MSSICAMRSLLAASTFLRSGASPLLRPLSRPLPSRLNLSRFGPVRPVSAAAAAADKSRGGGG

SAMEAQPSYPGEIHVIVGPMFAGKTTALLRRVQVEAGTGRNVALIKSDKDNRYGLDSVVTHD

GTKMPCWALPELSSFQDKLGTEAYDKVDVIGIDEAQFFDDLHDFCCKAADRDGKIVVVAGLD

GDYKRNKFGSVLDIIPLADSVTKLTARCELCGRRAFFTLRKTRETKTELIGGADVYMPVCRQ

HYLDGQIVIEATRIVLDLEKSKVIHAFK

*A. thaliana* TK1 AAF13097
(SEQ ID NO 15)
MATLKASFLIKTLDSDVTGDFLSDLERRGSGAVHVIMGPMFSGKSTSLLRRIKSEISDGR

SVAMLKSSKDTRYAKDSVVTHDGIGFPCWALPDLMSFPEKFGLDAYNKLDVIGIDEAQFF

GDLYEFCCKVADDDGKIVIVAGLDGDYLRRSFGAVLDIIPIADSVTKLTARCEVCGHKAF

FTLRKNCDTRTELIGGADVYMPVCRKHYITNHIVIKASKKVLEDSDKARAESCVAATI

*A. thaliana* TK1b
(SEQ ID NO 16)
MRTLISPSLAPFSLHLHKPSLFSTALRFSFSINNITPTNSPPSTISTRKLQTKATRVTSS

SSSQPLSSSSPGEIHVVVGPMFSGKTTTLLRRILAERETGKRIAIIKSNKDTRYCTESIV

THDGEKYPCWSLPDLSSFKERFGFDDYENRLDVIGIDEAQFFGDLYEFCREAADKEGKTV

IVAGLDGDFMRRRFGSVLDLIPIADTVTKLTSRCEVCGKRALFTMRKTEEKETELIGGAE

VYMPVCRSHYVCGQNVLETARAVLDSSNNHSVVASSL

Tomato dCGK
(SEQ ID NO 17)
MVEFLQSSIGIIHRNHAESITTYIRKSVDEELKENNSDS

NVKSTQKKRLTFCVEGNISVGKTTFLQRIANETLELQDLVEIVPEPIAKWQDIGPDHFNI

LDAFYAEPQRYAYTFQNYVFVTRVMQERESSGGIRPLRLMERSVFSDRMVFVRAVHEANW

MNEMEISIYDSWFDPVVSTLPGLIPDGFIYLRASPDTCHKRMMLRKRTEEGGVSLEYLRG

LHEKHESWLFPFESGNHGVLSVSELPLNFDKFCVPPEIRDRVFYLEGNHMHPSIQKVPAL

VLDCEPNIDFNRDIEAKRQYARQVADFFEFVKKKQEVMPGAGEEQPKGNQAPVMLPQNGG

LWVPGGKFSESTLNLDFRRNMSFMSH

The corresponding nucleotide sequences can be found in Genbank using the accession numbers given above, in the references given above and for the plant kinases in WO 03/100045 (thymidine kinases), and WO 2004/003185 (dCK/dGK).

In a preferred embodiment, the deoxyribonucleoside kinase is selected from the group consisting of
a) a deoxyribonucleoside kinase having the amino acid sequence of any of SEQ ID No 1 to 17;
b) a deoxyribonucleoside kinase variant comprising an amino acid sequence having at least 50% sequence identity to any of SEQ ID No 1 to 17;
c) a deoxyribonucleoside kinase encoded by a nucleotide sequence capable of hybridising under conditions of high stringency to a nucleotide sequence encoding any of SEQ ID No 1 to 17.

In the context of this invention, the term kinase variant is a polypeptide (or protein) having an amino acid sequence that differs from the sequence presented as SEQ ID NO: 1, as SEQ ID NO:2, as SEQ ID NO: 3, as SEQ ID NO: 4, as SEQ ID NO: 5, as SEQ ID NO: 6, as SEQ ID NO: 7, as SEQ ID NO: 8, as SEQ ID NO: 9, as SEQ ID NO: 10, as SEQ ID NO: 11, as SEQ ID NO: 12, as SEQ ID NO: 13, as SEQ ID NO: 14, as SEQ ID NO: 15, as SEQ ID NO: 16, as SEQ ID NO: 17, at one or more amino acid positions and has dNK activity. Such analogous polypeptides include polypeptides comprising conservative substitutions, splice variants, isoforms, homologues from other species, and polymorphisms.

As defined herein, the term "conservative substitutions" denotes the replacement of an amino acid residue by another, biologically similar residue. Examples of conservative substitutions include
(i) the substitution of one non-polar or hydrophobic residue such as alanine, leucine, isoleucine, valine, proline, methionine, phenylalanine or tryptophan for another, in particular the substitution of alanine, leucine, isoleucine, valine or proline for another; or
(ii) the substitution of one neutral (uncharged) polar residue such as serine, threonine, tyrosine, asparagine, glutamine, or cysteine for another, in particular the substitution of arginine for lysine, glutamic for aspartic acid, or glutamine for asparagine; or
(iii) the substitution of a positively charged residue such as lysine, arginine or histidine for another; or
(iv) the substitution of a negatively charged residue such as aspartic acid or glutamic acid for another.

Modifications of this primary amino acid sequence may result in proteins which have substantially equivalent activity as compared to the unmodified counterpart polypeptide, and thus may be considered functional analogous of the parent proteins. Such modifications may be deliberate, e.g. as by site-directed mutagenesis, or they may occur spontaneous, and include splice variants, isoforms, homologues from other species, and polymorphisms. Such functional analogous are also contemplated according to the invention.

It has been found that deoxyribonucleoside kinase enzymes that are C- and/or N-terminally altered significantly change their properties in particular in respect of kinetic properties such as turnover and substrate specificity. So from having a more restricted specificity, usually deoxycytidine kinase (dCK) and deoxyguanosine kinase (dGK) activity, the deoxyribonucleoside kinase enzymes of the invention may be converted into essentially multi-substrate enzymes, having ability to phosphorylate all four deoxyribonucleosides.

A variant deoxyribonucleoside kinase can be defined with reference to the amino acid sequence of a known deoxyribonucleoside kinase, such as any of the kinases disclosed above. In a preferred embodiment, the variant kinase has at least 50% sequence identity to a reference sequence, more preferably at least 60% sequence identity, more preferably at least 70% sequence identity, more preferably at least 75% sequence identity, more preferably at least 80% sequence identity, more preferably at least 85% sequence identity, more preferably at least 90% sequence identity, more preferably at least 95% sequence identity. The individual reference sequence may be either of SEQ ID NO: 1, SEQ ID NO:2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

In a more preferred embodiment, the deoxyribonucleoside kinases comprise a deoxyribonucleoside kinase selected from the group consisting of
a) a deoxyribonucleoside kinase having the amino acid sequence of any of SEQ ID NO 1 to 5; and
b) a deoxyribonucleoside kinase variant comprising an amino acid sequence having at least 70% sequence identity to any of SEQ ID No 1 to 5 and having dNK activity.

It is also possible to administer two or more deoxyribonucleoside kinases to the same individual.

Without being limiting the following combinations of kinase and nucleoside analogues are preferred:
HSV-tk—GCV, ACV, penciclovir
*Drosophila melanogaster* dNK or B5—gemcitabine, CdA, FaraA, araC, ddC
Plant TKs including Tomato TK-AZT, D4T, ddT, fluorouridine
Plant dNKs including *Arabidopsis thaliana* dNK-gemcitabine, CdA, FaraA, araC, ddC.

A preferred, non-limiting example of a mathematical algorithm utilized for the comparison of sequences and calculation of sequence identities is the algorithm of Myers and Miller, CABIOS (1989). Such an algorithm is incorporated into the ALIGN program (version 2.0) which is part of the FASTA sequence alignment software package (Pearson W R, Methods Mol Biol, 2000, 132:185-219). Align calculates sequence identities based on a global alignment. Align0 does not penalise to gaps in the end of the sequences. When utilizing the ALIGN or Align0 program for comparing amino acid sequences, a BLOSUM50 substitution matrix with gap opening/extension penalties of −12/−2 is preferably used.

Encapsulation

Encapsulated cell therapy is based on the concept of isolating cells from the recipient host's immune system by surrounding the cells with a semipermeable biocompatible material before implantation within the host. The invention includes a device in which cells of the invention are encapsulated in an immunoisolatory capsule. An "immunoisolatory capsule" means that the capsule, upon implantation into a recipient host, minimises the deleterious effects of the host's immune system on the cells in the core of the device. Cells are immunoisolated from the host by enclosing them within implantable polymeric capsules formed by a microporous membrane. This approach prevents the cell-to-cell contact between host and implanted tissues, eliminating antigen recognition through direct presentation. The membranes used can also be tailored to control the diffusion of molecules, such as antibody and complement, based on their molecular weight while allowing for the diffusion of a therapeutic protein. Using encapsulation techniques, cells can be transplanted into a host without immune rejection, either with or without use of immunosuppressive drugs. Useful biocompatible polymer capsules usually contain a core that contains cells, either suspended in a liquid medium or immobilised within an immobilising matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated cells from immune destruction. The semipermeable nature of the capsule membrane also permits the biologically active molecule of interest to easily diffuse from the capsule into the surrounding host tissue.

The capsule can be made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics. Preferably the capsule of this invention will be similar to those described by WO 92/19195 or WO 95/05452, incorporated by reference; or U.S. Pat. Nos. 5,639,275; 5,653,975; 4,892,538; 5,156,844; 5,283,187; or U.S. Pat. No. 5,550,050, incorporated by reference. Such capsules allow for the passage of metabolites, nutrients and therapeutic substances while minimizing the detrimental effects of the host immune system. Components of the biocompatible material may include a surrounding semipermeable membrane and the internal cell-supporting scaffolding. Preferably, the recombinant cells are seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene teraphthalate, nylon, polyamides, polyurethanes, polybutester, silk, cotton, chitin, carbon, or biocompatible metals. Also, bonded fiber structures can be used for cell implantation (U.S. Pat. No. 5,512,600, incorporated by reference). Biodegradable polymers include those comprised of poly(lactic acid) PLA, poly(lactic-coglycolic acid) PLGA, and poly(glycolic acid) PGA and their equivalents. Foam scaffolds have been used to provide surfaces onto which transplanted cells may adhere (WO 98/05304, incorporated by reference). Woven mesh tubes have been used as vascular grafts (WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

The jacket preferably has a molecular weight cutoff of less than 1000 kD, more preferably between 50-700 kD, most preferably between 70-300 kD. The molecular weight cutoff should be selected to ensure that the bioactive therapeutic protein can escape from the capsule while protecting the encapsulated cells from the immune system of the patient.

The thickness of the jacket typically lies in the range of 2 to 200 microns, more preferably from 50 to 150 microns. The jacket should have a thickness to give the capsule sufficient strength to keep the cells encapsulated and should with this in mind be kept as thin as possible to take up as little space as possible.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fiber membrane. Such membranes, and methods of making them are disclosed by U.S. Pat. Nos. 5,284,761 and 5,158,881, incorporated by reference. The surrounding semipermeable membrane may be formed from a polyether sulfone hollow fiber, such as those described by U.S. Pat. No. 4,976,859 or U.S. Pat. No. 4,968,733, incorporated by reference. An alternate surrounding semipermeable membrane material is poly (acrylonitrile/covinyl chloride).

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations, which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired. A particularly preferred shape is cylinder-shaped as such a shape is easily produced from hollow fibers which can produces industrially.

When macrocapsules are used, preferably at least $10^3$ cells are encapsulated, such as between $10^3$ and $10^8$ cells are encapsulated, most preferably $10^5$ to $10^7$ cells are encapsulated in each device. Of course, the number of cells in each capsule depends on the size of the capsule. As a rule of thumb, in a capsule with foam (described below) the present inventors have found that loading between 10,000 and 100,000 cells per μL of capsule (volume calculated as the internal volume including foam), more preferably from 25,000 to 50,000 cells per μL, more preferably from 30,000 to 40,000 cells per μL. The number of cells to be loaded also depends on the size of the cells.

Dosage may be controlled by implanting a fewer or greater number of capsules, preferably between 1 and 10 capsules per patient.

A macrocapsule in the present context is a capsule having a volume of at least 1 μL, such as from 1 to 10 μL.

The scaffolding may be coated with extracellular matrix (ECM) molecules. Suitable examples of extracellular matrix molecules include, for example, collagen, laminin, and fibronectin. The surface of the scaffolding may also be modified by treating with plasma irradiation to impart charge to enhance adhesion of cells.

Any suitable method of sealing the capsules may be used, including the use of polymer adhesives or crimping, knotting and heat sealing. In addition, any suitable "dry" sealing method can also be used, as described, e.g., in U.S. Pat. No. 5,653,687, incorporated by reference.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148, incorporated by reference), and the aqueous and vitreous humors of the eye (see WO 97/34586, incorporated by reference).

Foam Scaffolds:

The foam scaffold may be formed from any suitable material that forms a biocompatible foam with an open cell or macroporous structure with a network of pores. An open-cell foam is a reticulate structure of interconnected pores. The foam scaffold provides a non-biodegradable, stable scaffold material that allows attachment of adherent cells. Among the polymers that are useful in forming the foam scaffolds for the devices of this invention are thermoplastics and thermoplastic elastomers.

Some examples of materials useful in forming suitable foam scaffolds are listed in Table 1.

TABLE 1

| Thermoplastics: | Thermoplastic Elastomers: |
|---|---|
| Acrylic | Polyamide |
| Modacrylic | Polyester |
| Polyamide | Polyethylene |
| Polycarbonate | Polypropylene |
| Polyester | Polystyrene |
| Polyethylene | Polyurethane |
| Polypropylene | Polyvinyl Alcohol |
| Polystyrene | Silicone |
| Polysulfone | |
| Polyethersulfone | |
| Polyvinylidene fluoride | |

Thermoplastic foam scaffolds made from polysulfone and polyethersulfone, and thermoplastic elastomer foam scaffolds made from polyurethane and polyvinyl alcohol are preferred.

The foam must have some (but not necessarily all) pores of a size that permits cells to attach to the walls or surfaces within the pores. The pore size, pore density and void volume of the foam scaffold may vary. The pore shape may be circular, elliptical or irregular. Because the pore shape can vary considerably, its dimensions may vary according to the axis being measured. For the purposes of this invention, at least some pores in the foam should have a pore diameter of between 20-500 μm, preferably between 50-150 μm. Preferably the foregoing dimensions represent the mean pore size of the foam. If non-circular, the pore may have variable dimensions, so long as its size is sufficient to permit adherent cells to attach to the walls or surfaces within the pore. In one embodiment, foams are contemplated having some elliptical pores that have a diameter of 20-500 μm along the minor axis and a diameter of up to 1500 μm along the major axis.

In addition to the foregoing cell permissive pores sizes, preferably a least a fraction of the pores in the foam should be less than 10 µm to be cell impermissive but still provide channels for transport of nutrients and biologically active molecules throughout the foam.

Pore density of the foam (i.e., the number per volume of pores that can accommodate cells, as described above) can vary between 20-90%, preferably between 50-70%.

Similarly, the void volume of the foam may vary between 20-90%, preferably between 30-70%.

The walls or surfaces of the pores are typically coated with an extracellular matrix molecule or molecules, or other suitable molecule. This coating can be used to facilitate adherence of the cells to the walls of the pores, to hold cells in a particular phenotype and/or to induce cellular differentiation.

Preferred examples of extracellular matrix molecules (ECM) that can be adhered to the surfaces within the pores of the foams include: collagen, laminin, vitronectin, polyornithine and fibronectin. Other suitable ECM molecules include glycosaminoglycans and proteoglycans; such as chrondroitin sulfate, heparin sulfate, hyaluron, dermatan sulfate, keratin sulfate, heparan sulfate proteoglycan (HSPG) and elastin.

The ECM may be obtained by culturing cells known to deposit ECM, including cells of mesenchymal or astrocyte origin. Schwann cells can be induced to synthesize ECM when treated with ascorbate and cAMP. See, e.g., Baron-Van Evercooren et al., "Schwann Cell Differentiation in vitro: Extracellular Matrix Deposition and Interaction," Dev. Neurosci., 8, pp. 182-96 (1986).

In addition, adhesion peptide fragments, e.g., RGD containing sequences (ArgGlyAsp), YIGSR-containing sequences (TyrlleGlySerArg) (SEQ ID NO: 18), as well as IKVAV containing sequences (IleLysValAlaVal) (SEQ ID NO: 19), have been found to be useful in promoting cellular attachment. Some RGD- containing molecules are commercially available e.g., PepTite-2000.TM. (Telios).

The foam scaffolds of this invention may also be treated with other materials that enhance cellular distribution within the device. For example, the pores of the foam may be filled with a non-permissive hydrogel that inhibits cell proliferation or migration. Such modification can improve attachment of adherent cells to the foam scaffold. Suitable hydrogels include anionic hydrogels (e.g., alginate or carageenan) that may repel cells due to charge. Alternately, "solid" hydrogels (e.g., agarose or polyethylene oxide) may also be used to inhibit cell proliferation by discouraging binding of extracellular matrix molecules secreted by the cells.

Treatment of the foam scaffold with regions of a non-permissive material allows encapsulation of two or more distinct cell populations within the device without having one population overgrow the other. Thus non-permissive materials may be used within the foam scaffold to segregate separate populations of encapsulated cells. The distinct populations of cells may be the same or different cell types, and may produce the same or different biologically active molecules. In one embodiment, one cell population produces a substance that augments the growth and/or survival of the other cell population. In another embodiment, multiple cell types producing multiple biologically active molecules are encapsulated. This provides the recipient with a mixture or "cocktail" of therapeutic substances.

The devices of this invention may be formed according to any suitable method. In one embodiment, the foam scaffold may be pre-formed and inserted into a pre-fabricated jacket, e.g., a hollow fiber membrane, as a discrete component.

Any suitable thermoplastic or thermoplastic elastomer foam scaffold material may be preformed for insertion into a pre-fabricated jacket. In one embodiment we prefer polyvinyl alcohol (PVA) sponges for use as the foam scaffold. Several PVA sponges are commercially available. For example, PVA foam sponges #D-3, 60 µm pore size are suitable (Rippey Corp, Kanebo). Similarly, PVA sponges are commercially available from Ivalon Inc. (San Diego, Calif.). PVA sponges are water-insoluble foams formed by the reaction of aerated Poly(vinyl alcohol) solution with formaldehyde vapor as the crosslinker. The hydroxyl groups on the PVA covalently crosslink with the aldehyde groups to form the polymer network. The foams are flexible and elastic when wetted and semi-rigid when dried.

As an alternative, support a mesh or yarn may be used as described in U.S. Pat. No. 6,627,422. For easy retrieval the capsule may be equipped with a tether anchor.

NGC-407 or NGC-407 derived cells of the invention can be expanded as described in the examples and be loaded into the immunoisolatory capsule. After loading, the capsules can be kept for a number of weeks in vitro. During this period the growth medium may be one that allows continued proliferation within the capsule—to fill the capsule more completely—or the medium may be replaced by a differentiation medium to differentiate the encapsulated cells and thereby stop the proliferation.

Support Matrix for Cells of the Invention

The method of the present invention further comprises the culturing of the cells of the invention in vitro on a support matrix prior to implantation into the mammalian brain. The preadhesion of cells to microcarriers prior to implantation in the brain is designed to enhance the long-term viability of the transplanted cells and provide long term functional benefit. Methods for culturing cells on a support matrix and methods for implanting said cells into the brain are described in U.S. Pat. No. 5,750,103 (Cherksey).

To increase the long term viability of the transplanted cells, the cells to be transplanted can be attached in vitro to a support matrix prior to transplantation. Materials of which the support matrix can be comprised include those materials to which cells adhere following in vitro incubation, and on which cells can grow, and which can be implanted into the mammalian body without producing a toxic reaction, or an inflammatory reaction which would destroy the implanted cells or otherwise interfere with their biological or therapeutic activity. Such materials may be synthetic or natural chemical substances, or substances having a biological origin.

The matrix materials include, but are not limited to, glass and other silicon oxides, polystyrene, polypropylene, polyethylene, polyvinylidene fluoride, polyurethane, polyalginate, polysulphone, polyvinyl alcohol, acrylonitrile polymers, polyacrylamide, polycarbonate, polypentent, nylon, amylases, natural and modified gelatin and natural and codified collagen, natural and modified polysaccharides, including dextrans and celluloses (e.g., nitrocellulose), agar, and magnetite. Either resorbable or non-resorbable materials may be used. Also intended are extracellular matrix materials, which are well-known in the art. Extracellular matrix materials may be obtained commercially or prepared by growing cells which secrete such a matrix, removing the secreting cells, and allowing the cells which are to be transplanted to interact with and adhere to the matrix. The matrix material on which the cells to be implanted grow, or with which the cells are mixed, may be an indigenous product of the cells. Thus, for example, the matrix material may be extracellular matrix or basement membrane material, which is produced and secreted by cells to be implanted.

To improve cell adhesion, survival and function, the solid matrix may optionally be coated on its external surface with factors known in the art to promote cell adhesion, growth or survival. Such factors include cell adhesion molecules, extracellular matrix, such as, for example, fibronectin, laminin, collagen, elastin, glycosaminoglycans, or proteoglycans or growth factors.

Alternatively, if the solid matrix to which the implanted cells are attached is constructed of porous material, the growth- or survival promoting factor or factors may be incorporated into the matrix material, from which they would be slowly released after implantation in vivo.

When attached to the support according to the present invention, the cells used for transplantation are generally on the "outer surface" of the support. The support may be solid or porous. However, even in a porous support, the cells are in direct contact with the external milieu without an intervening membrane or other barrier. Thus, according to the present invention, the cells are considered to be on the "outer surface" of the support even though the surface to which they adhere may be in the form of internal folds or convolutions of the porous support material which are not at the exterior of the particle or bead itself.

The configuration of the support is preferably spherical, as in a bead, but may be cylindrical, elliptical, a flat sheet or strip, a needle or pin shape, and the like. A preferred form of support matrix is a glass bead. Another preferred bead is a polystyrene bead.

Bead sizes may range from about 10 pm to 1 mm in diameter, preferably from about 90 μm to about 150 μm. For a description of various microcarrier beads, see, for example, Fisher Biotech Source 87-88, Fisher Scientific Co., 1987, pp. 72-75; Sigma Cell Culture Catalog, Sigma Chemical Co., St, Louis, 1991, pp. 162-163; Ventrex Product Catalog, Ventrex Laboratories, 1989; these references are hereby incorporated by reference. The upper limit of the bead's size may be dictated by the bead's stimulation of undesired host reactions, which may interfere with the function of the transplanted cells or cause damage to the surrounding tissue. The upper limit of the bead's size may also be dictated by the method of administration. Such limitations are readily determinable by one of skill in the art.

EXAMPLES

Example 1

Generation and Characterisation of the NGC-407 Cell Line

This example illustrates the generation and in vitro characterisation of the NGC-407 cell line.

Human midbrain cells in primary culture were prepared from first trimester human fetal brain (obtained through Lund University, Sweden). The tissue was procured in compliance with Swedish laws and regulations. Immediately after dissection of the ventral midbrain, the tissue was cut into <0.5 mm$^3$ pieces by placing the tissue in a drop of Cell dissociation solution (Sigma #C5914) in a petri dish. The tissue was then cut by moving two scalpels against each other. Tissue was transferred to 2 ml culture medium consisting of DMEM/F12 (Gibco #31331-028), N2 supplement (Gibco #17502-048) supplemented with 0.5% HSA (Sigma #A 1653), 0.6% Glucose (Sigma #G8769), 5 mM HEPES (Gibco #15630-056), B27 supplement (Gibco #17504-044), 40 μg/ml bFGF (R&D Systems #233-FB) 20 ug/ml EGF (R&D Systems #236-EG), centrifugated at 1,000 rpm for 5 minutes and respuspended in fresh culture medium. Tissue pieces were seeded into 1-4 wells in PLL/Fibronectin coated 4 w chamberslides or 24 w plates. Standard cell culture plastic was used and PLL/fibronectin coating performed according to:

Coating of Culture Vessels:
1. Incubate with 0.01% Poly-L-lysine solution (Sigma #P4832) for 1 h at 37° C.
2. Remove PLL, rinse with dH$_2$O (Gibco #15230-071) and let the surface dry for 2 h.
3. Just before seeding the cells, add enough solution of fibronectin (Sigma #F0895) diluted to 50 μg/ml in dH$_2$O to cover surface, aspirate immediately, and let the surface dry for 45 min before adding the tissue/cells.

Figure 5:
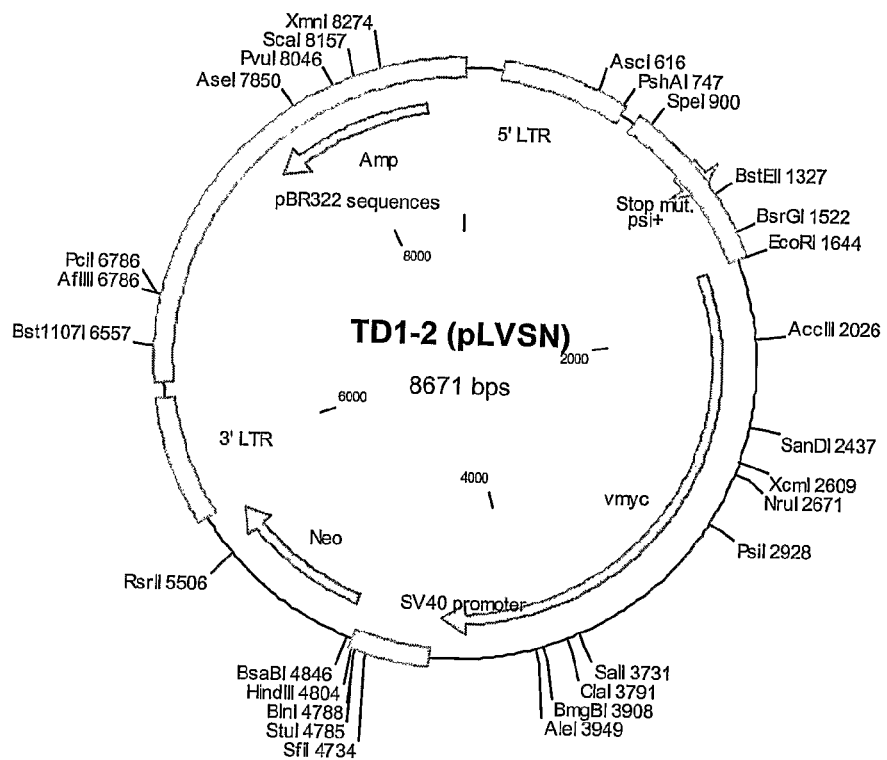
FIG. 5. Vector map of the TD1-2 immortalisation vector used for immortalising NGC-407 cell line.

At 4 days after seeding the cell cultures were transduced with the TDI-2 retroviral vector by adding viral stock at an MOI of 1, incubated overnight and removed by changing culture medium. The vector TDI-2 was made by cloning v-myc (as a gag-vmyc fragment) (GenBank Acc. #: AF033809) as an EcoRI/DraI fragment between EcoRI and HpaI sites of pLXSN (BD Clontech, cat #: 631509, GenBank Acc. #: M28248) (FIG. 5). A gene conferring neomycin resitance is also present in the vector. The culture was expanded in culture medium and PLL/fibronectin coated vessels to a confluent T25 flask. Geneticin at a concentration of 800 μg/ml was added for selection of transduced cells. After selection, cultures were maintained growing as monolayer in the culture medium described above. Cultures approaching confluence were passaged using a cell scraper and split 1:4 every 3-7 days.

Figure 2:
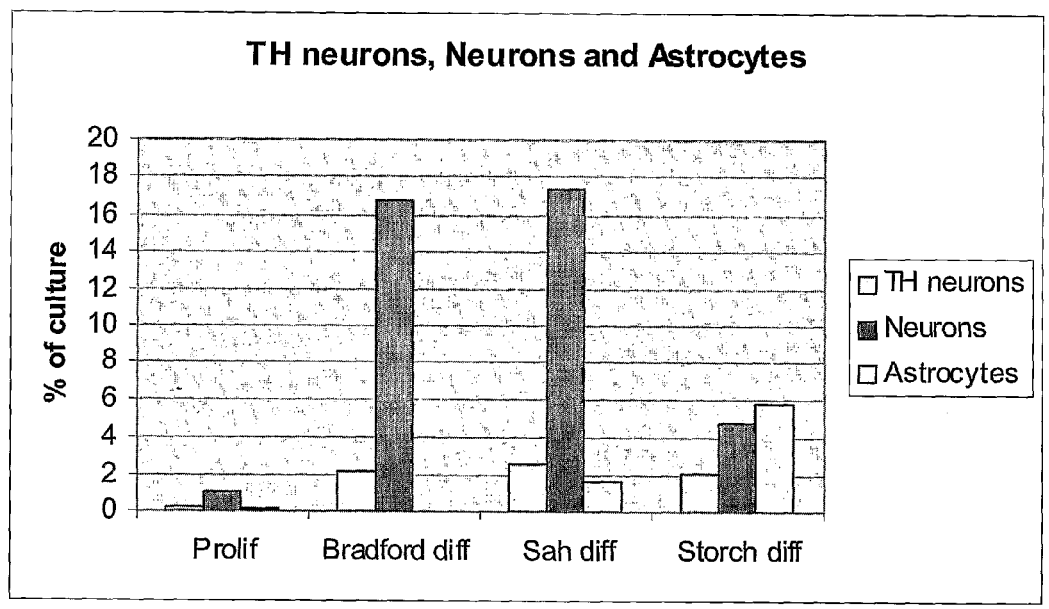
FIG. 2 shows a diagram of the percentage of differentiated NGC-407 cells labelled with the different markers. TH neurons are cells labelled with the TH antibody, neurons are cells labelled with the β-III-tubulin antibody and astrocytes are cells labelled with the GFAP antibody. The diagram shows four different groups; proliferating cells (Prolif) and three groups differentiated with the three differentiation protocols according to Riaz et al (Bradford diff), Sah et al (Sah diff) and Storch et al (Storch diff).
Figure 3:
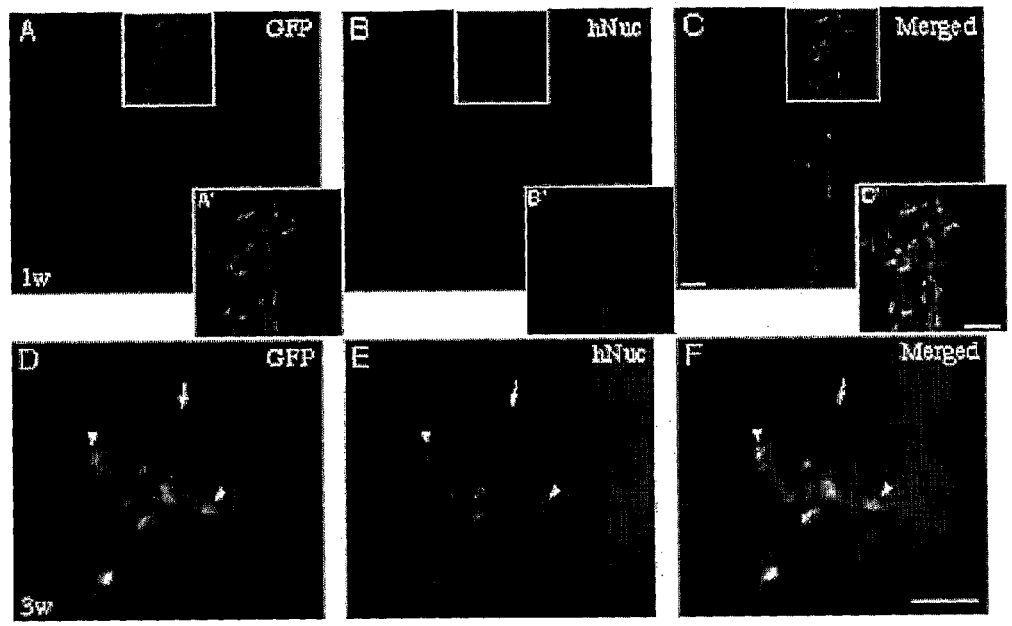
FIG. 3 shows immunohistochemical visualization of hNuc- and GFP-expressing NGC-407 cells at 1 and 3 weeks following transplantation to the rat striatum. At 1 week, a majority of the hNuc-positive cells were found around the site of injection, however, some cells had migrated away (B). GFP-staining revealed that approximately 50% of the hNuc-positive cells co-expressed GFP, and that the cells exhibit an astrocytic morphology (A, C and A', C'). A'-C' are close ups of the cell-populations represented in white boxes in A-C. At 3 weeks, a high percentage (>35%) of the hNuc-positive cells were still expressing the transgene (arrowheads) and displayed a more differentiated morphology (D-F). Arrows in D-F demonstrate a hNuc-positive cell, negative for GFP. Scale bars in C, C' and F represents 50 μm.

Removal of growth factors bFGF and EGF results in differentiation of the cell line. Addition of different factor will also influence the composition of cell phenotypes after differentiation (FIGS. 1 and 2). Three different differentiation media were used:
1. Culture medium with mitogenic growth factors bFGF and EGF replaced by 50 ng/ml BDNF, 20 ng/ml CNTF, 100 ng/ml IGF-1 and 50 uM Forskolin (Sah et al, 1997).
2. Culture medium with mitogenic growth factors bFGF and EGF replaced by 50 ng/ml BDNF, 50 uM Forskolin and 50 uM Dopamine (Bradford; Riaz et al, 2002).
3. Culture medium with mitogenic growth factors bFGF and EGF replaced by 10% FCS, 100 pg/ml IL-1b 1 ng/ml IL-11, 1 ng/ml LIF, 10 ng/ml GDNF (Storch et al, 2001).

Following differentiation, TH (tyrosine hydroxylase), β-III-tubulin, and GFAP (Glial fibrillary acidic protein) immunoreactive cells were observed. For such immunocytochemistry, cells were fixed in 4% paraformaldehyde, and were incubated with primary antibody (TH antibody Chemicon #AB152, GFAP antibody DAKO #Z0334, β-III-tubulin antibody Sigma #T-8660) in blocking buffer for 2 hours at room temperature, rinsed and then incubated with a fluorophor-conjugated (FITC or Cy3, Jackson ImmunoResearch Laboratories Inc) species-specific secondary antibody in blocking buffer for another hour at room temperature. Cultures were then rinsed with PBS and coverslipped with DAKO mounting medium before cell counting and photographing representative fields. The percentage of different cell types varied depending on the type of factors used for differentiation the numbers of TH positive cells were around 2% of total cell number in the differentiation media. The number neurons (Beta-III-tubulin positive cells) varied between 4-17% and the GFAP positive astrocytes between 0-6%. The proliferating cell culture consistently had below 1% of cells immunolabeled with any of the markers (FIGS. 1 and 2).

These results indicate that the NGC-407 is a neural progenitor cell line that can differentiate into neurons, astrocytes and dopaminergic neurons.

REFERENCES

Riaz S S, Jauniaux E, Stern G M, Bradford H F, The controlled conversion of human neural progenitor cells derived from foetal ventral mesencephalon into dopaminergic neurons in vitro, Brain Res Dev Brain Res., 2002 May 30; 136(1):27-34.

Sah D W, Ray J, Gage F H, Bipotent progenitor cell lines from the human CNS, Nat Biotechnol 1997 June; 15(6):574-80

Storch A, Paul G, Csete M, Boehm B O, Carvey P M, Kupsch A, Schwarz J., Long-term proliferation and dopaminergic differentiation of human mesencephalic neural precursor cells, Exp Neurol. 2001 August; 170(2):317-25.

Example 2

Transplantation and In Vivo Transgene Expression of the NGC-407 Cell Line

This example illustrates lentiviral transduction, stability of transgene express ion and integration of the NGC-407 cell line after experimental transplantation into the rat brain.

NGC-407 cells were expanded according to the methods described in Example 1. Forty-eight hrs prior to transplantation, NGC-407 cells were transduced with a self-inactivated lentiviral vector expressing GFP (LV-GFP-SIN; Zufferey R et al, 1998). The multiple of infection of 1 was used, resulting in a 60-70% transduction rate. At the day for transplantation, the cells were washed three times, trypsinized, centrifuged for 5 min at 600 rpm and the cell pellet was resuspended in Hank's Balanced Salt Solution (HBSS; Gibco, Sweden). The cell number was estimated in a hemocytometer and prepared into a single cell suspension with a density of 50.000 cells/µl in HBSS.

A total of 40 adult female Sprague-Dawley rats (B&K Universal, Stockholm, Sweden) were housed three per cage with free access to food and water under a 12 hour light:dark cycle. All surgical procedures were approved by and performed according to the guidelines of the Ethical Committee for Use of Laboratory Animals at Lund University, Sweden. The animals were anaesthetized with halothane (2% in $O_2$) and placed into a stereotaxic frame (Kopf Instruments, Tujunga, Calif., USA). 100.000 cells were injected bilaterally into the striatum, using a 10 µl Hamilton syringe, at the following coordinates from the bregma according to Paxinos and Watson (Paxinos and Watson, 1986); anterior-posterior: ±1.2; medial-lateral: ±3.0 and dorso-ventral: −4.0 and −5.0, with the tooth bar set at 0.0 mm. For evaluation if GFP was transferred from the grafted cells to the host cells after transplantation, one animal received bilateral injections of cells, killed by repeated cycles of freeze-thawing. No GFP- or human nuclei (hNuc)-positive cells were found in these grafts (data not shown).

The first set of 12 animals, got immuno-suppression one and two days before surgery with betamethasone (20 mg/kg, Betapred™, Defiante Farmacêutica) and cyclosporine A (10 mg/kg, Sandimmun Neoral®, Novartis), respectively, while the second round of 17 animals only received cyclosporine A (15 mg/kg), started 2 days before surgery. The substances were given orally with a silicon-tipped plastic tube down the esophagus, every day until sacrifice.

At 3 days, 1 week, 2 weeks, and 3 weeks following transplantation the rats were deeply anaesthetized with pentobarbital and perfused as previously described (Ericson C et al, 2002) before sectioning on a freezing-stage microtome at 40 µm in 6 series. Light-field and fluorescent stainings were preformed as described elsewhere (Ericson C et al, 2002), and the primary antibodies used were: chicken-anti-GFP (1:5000; Chemicon), mouse-anti-hNuc (1:100; Chemicon), two glial markers; rabbit-anti-glial fibrillary acidic protein (GFAP; 1:5000; DAKO A/S) and mouse-anti-S100 (1:500; Sigma), the glial progenitor marker rabbit-anti-NG2 (1:200; Chemicon), the neuronal marker mouse-anti-NeuN (1:1000; Chemicon), two markers for immature neural cells and reactive astrocytes; rabbit-anti-nestin (1:200; Chemicon) and mouse-anti-vimentin (1:50; DAKO NS) and the early neuronal marker mouse-anti-βIII-tubulin (1:333; Sigma).

Total number of hNuc- and GFP-positive cells in the grafts were estimated by stereology using the optical fractionator formula (West M J, 1999) or by the Abercrombie formula (Abercrombie M, 1946), as previously described (Ericson C et al, 2002).

The grafted cells survived up to 3 weeks following transplantation, the longest time-point studied, detected by hNuc. Stereological estimations revealed a decrease of hNuc-expressing cells over the first 2 weeks, but the cell number was maintained at 3 weeks (NGC-407: 3 d, 3271±1866; 1 w, 3729±3715; 2 w, 1159±865; 3 w, 1207±1225). Moreover, at least 35% of the hNuc positive cells co-expressed GFP at all time-points (3d, 2358±1070 (72%); 1 w, 1487±821 (40%); 2 w, 560±403 (48%); 3 w, 425±275 (35%)).

In 12 animals, a higher number of GFP-expressing cells than hNuc-positive cells was detected, suggesting that hNuc did not detect all grafted cells. Thus, the low number of estimated hNuc-positive cells found in all grafts might be due to a down-regulation of hNuc expression, resulting in an unknown number of undetectable cells, and as a consequence an underestimation of the total number of grafted cells.

In conclusion, lentivirally transduced NGC-407 cells survive and integrate well following transplantation to the rat brain, without any signs of inflammation or tumor formation. A large percentage of the grafted cells expressed the transgene for up to at least 3 weeks.

REFERENCES

Abercrombie, M., Estimation of nuclear populations from microtome sections., Anat. Rec., 94 (1946) 239-247.

Ericson, C., Wictorin, K. and Lundberg, C., Ex vivo and in vitro studies of transgene expression in rat astrocytes transduced with lentiviral vectors, Exp Neurol, 173 (2002) 22-30.

Paxinos, G. and Watson, C., The rat brain in stereotxic coordinates., Academic Press, San Diego, 1986.

West, M. J., Stereological methods for estimating the total number of neurons and synapses: issues of precision and bias, Trends Neurosci, 22 (1999) 51-61.

Zufferey, R., Dull, T., Mandel, R. J., Bukovsky, A., Quiroz, D., Naldini, L. and Trono, D., Self-inactivating lentivirus vector for safe and efficient in vivo gene delivery, J Virol, 72 (1998) 9873-80.

Example 3

Gap-Junction Communication Between NGC-407 & U343MGa-cl 2:6 Cells and its Enhancement by 4-Phenyl Butyrate, Analyzed by Fluorescent Dye Transfer Methods Donor human embryonic neural stem cells (NGC-407) and recipient human glioblastoma cells (U343MGa-cl 2:6) were grown each in 2 separate 35 mm Petri dishes ($1\times10^5$/dish). For NGC-407 cells the plates were poly-L-lysine (Sigma) coated and the medium was DMEM/F12 1:1 with glutamax I (Invitrogen) containing 40 ng/ml bFGF2 (R&D Systems), 20 ng/ml rhEGF, 1× N2 supplement, 1× non-essential amino acid, 5 mM HEPES buffer solution (from Invitrogen), 0.5% human serum albumin and 6 g/L D-glucose (from Sigma). The recipient cells were grown in DMEM containing 10% FBS, 100 units/ml penicillin and 100 μg/ml streptomycin (from Invitrogen). When the cells were approx. 60% confluent, treatment with 0 & 0.5 mM 4-Phenyl Butyrate (PB) for donor cells and 0 & 4 mM PB for recipient cells was started and continued for 72 hours. The donor cells were then double labelled by incubating with 1 ml of cell medium containing 10 μM Dil and 5 μM Calcein-AM (Molecular Probes) for 20 min. After aspiration of the dye containing medium the cells were washed 4-5 times with pure medium and then with PBS to get rid of free dye. After a very brief trypsinization the cells were centrifuged and resuspended in co-culture medium (donor cell medium including 0.5% FBS). The medium of recipient cells was replaced by co-culture medium and $5 \times 10^4$ donor cells were added to one recipient plate. The PB treated donor cells were mixed with PB treated recipient cells and the treatment was continued in a 0.5 mM PB concentration. After 4 hours of co-culturing calcein dye transfer from donor to recipient cells was observed under an Olympus fluorescent microscope.

Results

Figure 4:
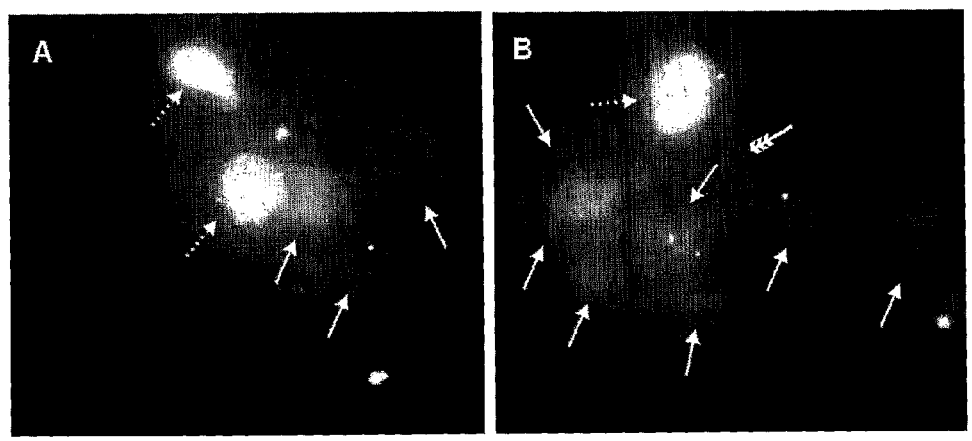
FIG. 4. A. Control cells Gap junction mediated transfer of calcein. Unlabeled U343MGa-cl 2:6 cells have become green (straight arrows) after receiving transferable calcein dye from the yellow (dotted arrows) double labeled (red DiI & green Calcein) NGC-407 cells. Both cell types are in physical contact with each other through extended processes. B. PB treated cells. The processes have become more prominent by PB treatment (triple arrow), and the number of green recipient cells has also been significantly increased in this group.

It was found that NGC-407 cells functionally communicated with U343MGa-cl 2:6 cells by forming gap junctional cell coupling and that the communication was significantly enhanced by 4-PB. See FIG. 4.

In another similar experiment, it was shown that the HDAC inhibitor 4-PB enhances the gap junction communication (GJC) between NGC-407 cells, as well as between NGC-407 cells and U87 gioblastoma cells. This was analyzed semi-quantitatively/qualitatively by using fluorescent dye transfer techniques. It is evident that the GJC is enhanced by 4-PB both under differentiating and proliferating conditions in vitro. This is relevant since the in vivo environment may present transplanted cells with conditions that stimulate neither differentiation nor proliferation.

Example 4

Migration of BrdU Labeled NGC-407-Cells Towards U87MG Glioblastoma Cell Xenograft In Vivo Method U87 cells (200.000 in 2 μl) were injected into the brain of nude rats, 3mm right lateral, 2 mm caudal from the bregma and 5 mm deep. U87-MG cells are available from ATCC under accession number HTB-14. After one week, when a tumour had been established, NGC-407 cells were prelabeled with 2 μM BrdU for 72 hours, and injected at a place 3 mm right lateral, 1 mm frontal from the bregma and 5 mm deep.

Two weeks after the stem cells injection, the animals were sacrificed, and the brain was sectioned (14 μm) and subjected to immunofluorescent staining using antibodies against BrdU and human nestin.

Results

A smaller number of BrdU labeled cells were found around the tumor border and inside the tumor. These cells were also positive for human nestin.

The results indicate a tropic migration of this neural progenitor cell line from the site of injection to the U87 cell tumor.

Example 5

Cloning Tomato TK1 Kinases into Retroviral Expression Vector for Stem Cells

Retroviral expression vector pLHCX (obtained from BD Biosciences Clontech, Catalog #K1061-1) which contains elements derived from Moloney murine leukemia virus (Mo-MuLV) and Moloney murine sarcoma virus (MoMuSV), and is designed for retroviral gene delivery and expression, was used for expression of the tomato TK1 kinase. The multiple cloning site of pLHCX was changed from HindIII-HpaI-ClaI to HindIII-XhoI-SalI-BamHI-SphI-MfeI-ClaI. The change was obtained by two oligonucleotides

```
                                        (SEQ ID NO: 20)
5'-AGCTTCTCGAGGTCGACGGATCCGCATGCCAATTGAT-'3
and
                                        (SEQ ID NO: 21)
5'-CGATCAATTGGCATGCGGATCCGTCGACCTCGAGA-'3
``` that were ligated into the HindII/ClaI cut pLHCX vector. The new polylinker of modified vector was named as pLHCXZ and was confirmed by DNA sequencing.

The tomato TK1 wild type and tomato TK1 deltaC gene (coding for a Tomato Thymidine kinase I with a C-terminal deletion of 26 amino acids, WO 03/100045) were cut out from pZG69 (TomTK1) and pZG59 (TomTK1ΔC26) (both described in WO 03/100045) respectively as XhoI/BglII fragments and cloned into the XhoI/BamHI site of the pLHCXZ vector. The construct containing the tomato TK1 wild type gene in pLHCXZ was named pZG556 and tomato TK1deltaC gene in pLHCXZ was named pZG561.

Example 6

Transduction of NGC-407 Cells with pZG556 and pZG561

Cell culture The human neuronal progenitor cell line NGC-407 was cultured in DMEM/F12 (Gibco #31331-028) conditioned with Human Serum Albunim (HSA) (Sigma #A 1653), N2 (Gibco #17502-048), B27 (Gibco #17504-044), Glucose (Sigma #G8769), bFGF (R&D Systems #233-FB), EGF (R& Systems #236-EG), MEM NEAA, x100 (Gibco #11140-035), HEPES (Gibco #15630-056), in poly-L-lysine (Sigma #P4832) coated flasks/Plates (CM-Lab, Denmark). Cells were grown at 37° C. and 5% $CO_2$ in a humidified incubator.

Construction of Retrovirus Vectors and Transduction Procedure

Mid scale production and concentration of Moloney Murine Leukemea Virus (MMLV)-derived replication defective VSV-G pseudo-typed retroviruses, typically yielding a total of $10^7$ transducing units, was performed in 293 T cells. The 293T packaging cells (ATTC CRL-11268) were cultured at 37° C., 5% $CO_2$ in OPTIMEM 1 medium (Life Technologies, Inc.).

The constructed pLHCXZ (Clontech) plasmid vector pZG561 (coding for a Tomato Thymidine kinase I with a C-terminal deletion of 26 amino acids, WO 03/100045) and pVPack-GP (Stratagene) plus pVPack-VSV-G (Stratagene) were transfected into the packaging cells using Lipo-fectAMINE PLUS (Invitrogen-Life Technologies, Inc.) according to the protocol provided by the supplier. The medium from the transfected cells, cultured in DMEM (Invitrogen), was collected 48 and 72 hours post transfection, filtered through a 0.45 μm filter, pelleted by ultracentrifugation (50.000g, 90 min at 4° C.) and dissolved in DMEM (Invitrogen). The titer of the virus was determined by reverse transcriptase assay. The virus was subsequently used to transduce the NGC-407 cell line.

Retroviral Transduction

The day before transduction, 1×10⁶ cells/well were seeded in 6-well plates. On the day of transduction, viruses were added with a MOI of 1. Cells incubated for 3 hours and thereafter media was renewed and cells were expanded and selected by addition of Hygromycin (Sigma #H3274) for 14 day. Subsequently cells were ready for experiments.

Cell Killing Effect of AZT in U87MG/Tomato Kinase Positive Cells

Exponentially growing NGC-407 wt and tomato kinase (ZG561) expressing cells were plated at a density of 5.000 cells/well in poly-L-lysine coated 96-well plates in 100 µl conditioned medium and incubated 37° C. in a humidified incubator with a gas phase of 5% $CO_2$. After 48 hours, medium was replaced with medium containing varying concentrations of AZT starting at 20 mM and down. Hereafter, cells were exposed to drug conditioned media for 120 constitutive hours. The chemo resistance of cultured cells was monitored by the surviving cell fraction as a function of the drug concentration. Viability of cells was determined via the colorimetric XTT assay (XTT kit II-Roche, cat no. 1465015). Briefly, cell media was carefully removed and 100 µl fresh media and 50 µl XTT mix was added to each well. The absorbance at 450 and 690 nm was determined using an ELISA plate reader (Ascent, ThermoLab). The $IC_{50}$ value (50% inhibition concentration) of the investigated compound was calculated as the mean value of each experiment using SigmaPlot® (Dyrberg Trading, DK).

Results

Figure 6A:
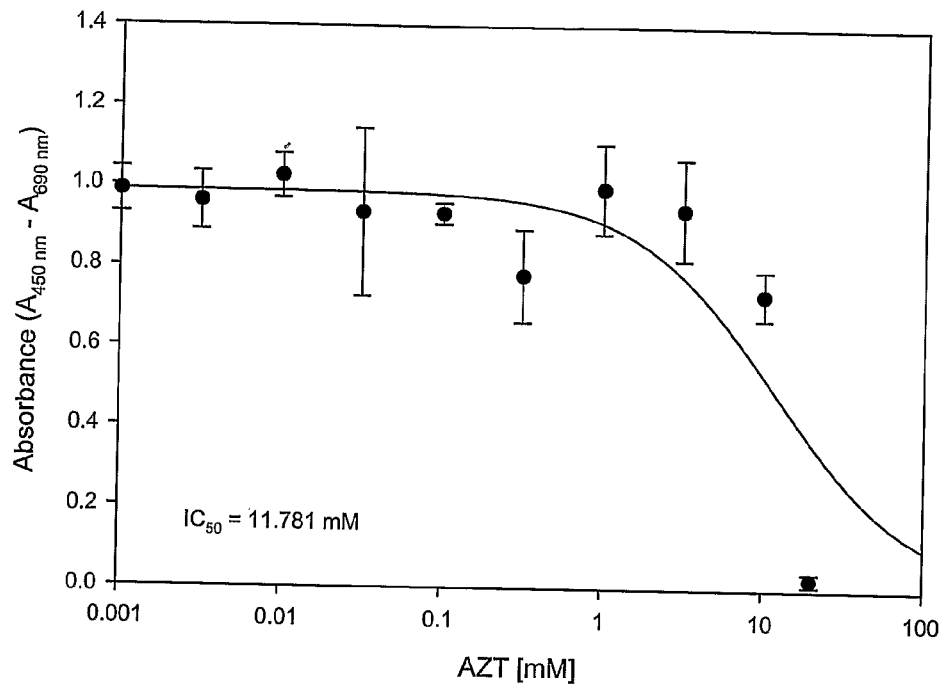
FIG. 6: $IC_{50}$ values for NGC-407 cell line (FIG. 6A) and Tomato thymidine kinase expressing NGC-407 cell line (FIG. 6B) with respect to AZT. For details, see Example 6.

The Hygromycin selected ZG561 and parental cells were tested for AZT activation. There was a significant sensitivity increase ($IC_{50}$ decrease), compared to the parental cell line (0.05105 mM and 11.781 mM, respectively), see FIGS. 6A and 6B.

Conclusion

The Tomato Thymidine kinase clearly sensitised the NGC-407 cells towards the nucleoside analogue AZT by a 230-fold order of magnitude, thus indicating a clinical relevance in a setting for glioma multiforme treatment in humans.

Example 7

Selection of Monoclones of Tomato TK1 Expressing NGC-407 Cells

Figure 6B:
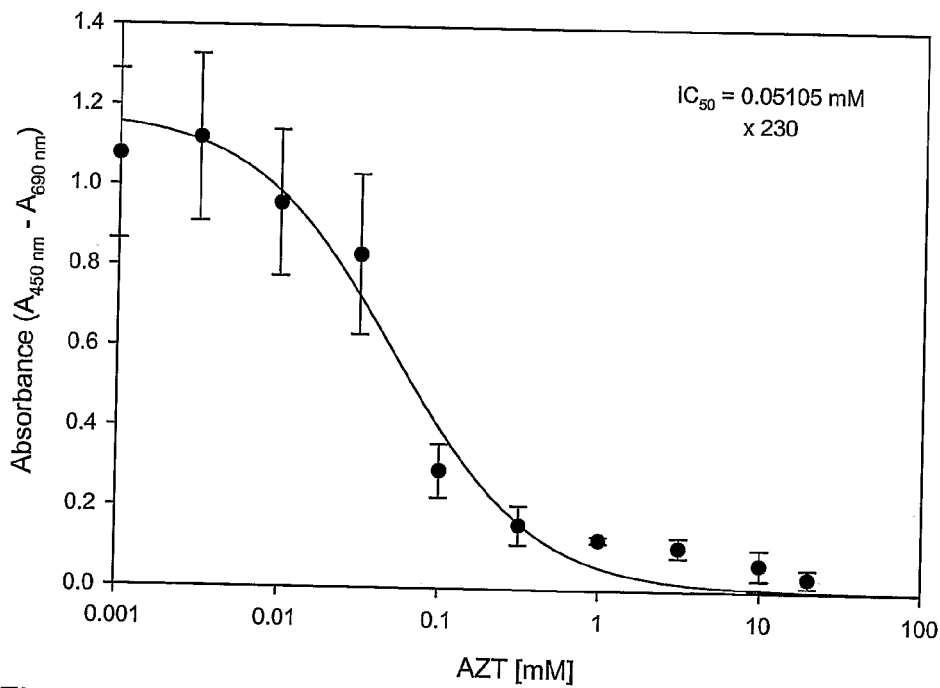

Monoclonal cell lines of tomato TK1 expressing NGC-407 cell lines were isolated and tested for enzymatic activity using thymidine and AZT as substrates. The best of the monoclonal cell lines possessed AZT activities twice as high as the activity of the polyclonal cell line expressing tomato TK1 (FIG. 6B).

Selection for Monoclones

Retro virally transduced NGC-407 cells expressing Tomato TK ΔC pLHCXZ (ZG561) (see example 6) were selected by addition of 100 µg Hygromycin/ml media for 14 day (Sigma #H3274). Hereafter cells were seeded in 4 poly-L-lysine coated 24-well plates at a cells density of 30 cells/well and placed in humidified incubator at 37° C., 5% $CO_2$. Media was changed regularly and after 21 days 32 clones were picked by pipeting and transferred to poly-L-lysine coated 6-well plates.

After expansion cells were cryo preserved and a pellet was prepared for kinase activity assay.

Thymidine Kinase Assay

The cells for activity assay were harvested and stored at −80° C. until activity testing. Cells were submitted to brief sonification in extraction buffer (50 mM Tris/HCl pH 7.5, 1 mM DTT, 10% (v/v) glycerol, 1% (v/v) Triton X-100, protease inhibitor cocktail (Complete™ from Roche Diagnostics) and thereafter thymidine kinase activity was determined in the cell extracts by initial velocity measurements based on four time samples by the DE-81 filter paper assay using tritium-labelled nucleoside substrates. App. 20 pg extracts were used in the assays. The assay was done as described by Munch-Petersen et al. [Munch-Petersen, B., Knecht, W, Lenz, C., Sondergaard, L. & Piskur, J: Functional expression of a multisubstrate deoxyribonucleoside kinase from *Drosophila melanogaster* and its C-terminal deletion mutants; *J. Biol. Chem.* 2000 275 6673-6679]. The deoxyribonucleosides were tested at a fixed concentration of 200 µM. One unit of deoxyribonucleoside kinase activity is defined as 1 nmol of the corresponding monophosphate formed per minute per mg of protein.

The protein concentration was determined according to Bradford with BSA as standard protein [Bradford M M: A rapid and sensitive method for the quantitation of microgram quantities of protein utilizing the principle of protein-dye binding; *Anal. Biochem.* 1976 72 248-254].

The results of these experiments are presented in Table 2 below.

TABLE 2

Thymidine kinase activity in crude extracts of NGC-407 monoclonal cells

|  | unit Thd | unit AZT | Thd ratio | AZT ratio |
| --- | --- | --- | --- | --- |
| Cl. 1 | 0.075 | 0.053 | 1.3 | 1.2 |
| Cl. 2 | 0.059 | 0.046 | 1.0 | 1.0 |
| Cl. 3 | 0.086 | 0.071 | 1.5 | 1.6 |
| Cl. 4 | 0.114 | 0.085 | 1.9 | 1.9 |
| Cl. 5 | 0.057 | 0.043 | 1.0 | 1.0 |
| Cl. 6 | 0.069 | 0.050 | 1.2 | 1.1 |
| Cl. 7 | 0.081 | 0.061 | 1.4 | 1.4 |
| Cl. 8 | 0.046 | 0.037 | 0.8 | 0.8 |
| Cl. 9 | 0.111 | 0.098 | 1.9 | 2.2 |
| Cl. 10 | 0.042 | 0.024 | 0.7 | 0.5 |
| Cl. 11 | 0.082 | 0.056 | 1.4 | 1.2 |
| Cl. 12 | 0.047 | 0.032 | 0.8 | 0.7 |
| Cl. 13 | 0.068 | 0.050 | 1.2 | 1.1 |
| Cl. 14 | 0.038 | 0.027 | 0.7 | 0.6 |
| Cl. 15 | 0.056 | 0.037 | 1.0 | 0.8 |
| Cl. 16 | 0.077 | 0.054 | 1.3 | 1.2 |
| Cl. 17 | 0.070 | 0.057 | 1.2 | 1.3 |
| Cl. 18 | 0.075 | 0.044 | 1.3 | 1.0 |
| Cl. 19 | 0.079 | 0.044 | 1.4 | 1.0 |
| Cl. 20 | 0.073 | 0.051 | 1.2 | 1.1 |
| Cl. 21 | 0.061 | 0.045 | 1.0 | 1.0 |
| Cl. 22 | 0.061 | 0.033 | 1.0 | 0.7 |
| Cl. 23 | 0.091 | 0.058 | 1.6 | 1.3 |
| Cl. 24 | 0.075 | 0.042 | 1.3 | 0.9 |
| NGC-407, ZG651 | 0.059 | 0.045 | 1.0 | 1.0 |
| NGC-407, parental | 0.016 | 0.014 | 0.3 | 0.3 |

Two monoclones (nr. 4 and nr. 9) exhibited higher phosphorylation activity of both thymidine and AZT compared to parental cells and cells transduced with ZG651.

Example 8

Comparison of NGC-407 to MESC2.10

Materials and Methods

The MESC2.10 human mesencephalic cell line (Lund University and Signal Pharmaceuticals Inc, LA Jolla, Calif., USA [Lotharius, J., et al., Effect of mutant alpha-synuclein on dopamine homeostasis in a new human mesencephalic cell line. J Biol Chem, 2002. 277(41): p. 38884-94]) was generated by dissecting the ventral mesencephalon from a 8-week-old human embryo and immortalized using a retroviral vector containing the v-myc oncogene under control of the tet-off system. MESC2.10 cells are cultured in DMEM/F12 containing N2 supplement (N2 medium) and basic fibroblast growth factor (bFGF) and differentiated by plating cells in differentiation medium consisting of N2 medium containing tetracycline ("differentiation in N2 medium"), or for dopaminergic differentiation in N2 medium containing tetracycline, dibutyryl cAMP (dbcAMP, Sigma), and glial cell line-derived neurotrophic factor (GDNF, RDsystems) ("DA differentiation medium").

The NGC-407 cell line was developed by dissecting the ventral mesencephalon from a 7-week-old human embryo, and immortalizing cells using a retroviral vector containing the v-myc oncogene. In this cell line the immortalizing gene is expressed constitutively in regular growth medium, and proliferation is controlled by changing the cell culture conditions. Thus, NGC-407 cells grow as an adherent monolayer in medium containing DMEM-F12 with N2 supplement +epidermal growth factor (EGF) and bFGF. When the cells are transferred into N2 medium without bFGF and EGF ("differentiation in N2 medium"), or for dopaminergic differentiation into N2 medium without bFGF and EGF and with GDNF and dbcAMP ("DA differentiation medium"), they start differentiate into neurons and astrocytes (see Table 3 for details).

Immunocytochemistry and Cell Counting

MESC2.10 and NGC-407 cell cultures differentiated for 4 days in parallel were fixed with 4% paraformaldehyde for 20 min at room temperature before immunocytochemical staining. Fixed cultures were pre-incubated with blocking buffer containing 5% normal goat serum and 0.3% Triton-X-100 and then incubated with one of the following antibodies, diluted in PBS containing 2% normal goat serum and 0.3% TritonX-100: mouse anti-tubulin β-III (1:750; Sigma), rabbit anti-GFAP (1:200; DAKO), rabbit anti-TH (1:400, Chemicon), or rabbit anti-nestin (1:200; chemicon). Incubations were carried out at 4° C. overnight. After washing, cultures were incubated with a fluorescin isothiocyanate (FITC)- or Texas red-conjugated species-specific secondary antibody, rinsed again and nuclear counterstained with 4,6-Diamidino-2-Phenylindole (DAPI, 1 µg/ml, Sigma). In order to quantify the percentage of TH-immunopositive cells out of the total population, cells were counted at 200× magnification, three fields were randomly chosen in each culture and the percentage of TH-immunopositive cells was calculated with respect to the total number of cells indicated by DAPI-positive nuclei. Data are from three independent experiments. On average, 400 cells were examined in each experiment.

Results of Cell Line Differentiation

Using immunocytochemistry, 2 human cell lines derived from the embryonic human VM at different stages of neuronal and dopaminergic differentiation were characterised. These immortalized cell lines can be expanded and cultured during long periods without uncontrolled transformation and will represent a homogenous, stable, reproducible source of cells. The percentage of TH-positive cells under the different differentiation protocols are shown in Table 3. TH-immunopositive neurons are detected in 19.1+/−0.2% of the differentiated MESC2.10 cells and 3.5+/−1.2% of the differentiated NGC-407 cells after 4 days in "DA differentiation medium", whereas only 0.6+/−0.1% of the MESC2.10 cells and 0.5+/−% of the NGC-407 cells were TH-positive after 4 days of "differentiation in N2 medium". NGC-407 has the capacity to differentiate into both βIII-tubulin-positive neurons (18.1$^{+}$/_4.9%) and GFAP-positive astrocytes (26.5$^{+}$/_4.0%), whereas MESC2.10 cells only give rise to βIII-tubulin-positive neurons (>90%). Thus, the polyclonal NGC-407 cell line can be described as a neural stem/progenitor cell line, and the MESC2.10 cell line as a unipotent neuronal progenitor cell line.

TABLE 3

Features of the two human mesencephalic cell lines employed in the study.

|  | MESC2.10 | NGC-407 |
|---|---|---|
| Donor Age | 8 weeks | 7 weeks |
| Immortalization construct | Tet-off v-myc | v-myc |
| Nestin/Vimentin | −/+ | +/+ |
| Neurons (βIII-tubulin+) | ~91% | 18.1 +/− 4.9% |
| Putative DA neurons (TH+) | 19.1% +/− 0.2% | 3.5 +/− 1.2% |
| Astrocytes (GFAP+) | ~0% | 26.5 $^{+}$/_ 4.0% |

Example 9

In Vivo Migration Studies of NGC-407 Cells in a Nude Rat Model of Human Glioblastoma Multiforme (Using U87MG Cell Line)

Materials & Methods 8-9 weeks old athymic nude male rats (rnu/rnu; Harlan, Germany) with an average weight of 200 g were used in our human glioblastoma multiforme xenograft model. They were housed in a group of 3 in standardized big cages in 50-70% relative humidity and 20°-24° C. temperature with 12/12 day/night variation. Food (Ad libitum), water and other materials used for these immunocompromised animals were autoclaved before use. Animals were anesthesitized by isoflurane inhalation and the head was fixed in a stereo tactic apparatus. Under microscopic guidance a burr hole of 1 mm diameter was made over the right hemisphere, 2 mm right lateral to the bregma. Using a Hamilton syringe of 5 µl volume $1.5 \times 10^5$ U87MG cells in 3 µl volume were slowly injected through the burr hole at a depth of 3.5 mm from the surface to reach the corpus callosum.

$2 \times 10^6$ neural progenitors (NGC-407) recombinantly expressing green fluorescent protein (GFP), were plated in a 100 mm Petri dish and were grown as neurospheres for 48 hours. They were collected, centrifuged and resuspended in 50 µl of growth medium. After one week of tumor cell implantation (to allow tumor growth) 3 µl of neurospheres were injected into each rat brain just contralateral to U87MG cells implantation. Half of the animals were treated intraperitoneally with PB 250 mg/kg body weight twice daily from the time of NSC inoculation and the rest got phosphate buffer saline as vehicle. All animals were observed twice daily for significant weight loss, abnormal behaviour or other neurological symptoms which were set as the end point of experiment. Otherwise, the treatment was continued for 2 weeks and the animals were then sacrificed by decapitation. Collected brain was immediately frozen in dry ice cooled 2-methyl butane and then kept in −75° C. freezer until they were sectioned by cryostat at 14 µm thickness.

Histopathological analysis of the sections was carried out by haematoxylin and eosin staining to determine the size and location of the implants. NGC-407 cells in the rat brain were tracked down by immunofluorescence studies using chicken anti-GFP antibody (Chemicon #AB16901). Immunohistochemically the tumor location was determined by correlating with the histological analysis and by the cell density while the sections were counter-stained with hoechst.

Results

The current results confirm previous in vitro results, and extend them to include in vivo migration of human NGC-407 neural stem cells.

The suicide gene therapeutic paradigm using NGC-407 cells recombinantly expressing a suicide gene, relies on their migration through the brain to the site of tumor, and the efficient transfer of activated prodrug to neighbouring tumor cells.

NGC-407 cells expressing green fluorescent protein, (GFP) implanted contralaterally of a formed xenograft tumor in nude rats were able to migrate through the corpus callosum to the tumor bed, and even inside the tumor. The treatment of the rats with intraperitoneally added 4-PB, during several days, enhanced the GFP staining around an inside the tumor. The interpretation of this is that more GFP-expressing cells were present around and in the tumor, emphasizing the future usefulness of these cells for the transfer of a suicide gene to the site of brain tumors. It can not be ruled however, that the enhanced GFP staining is due to induction by 4-PB of the CMV promoter driving the GFP gene.

The invention claimed is:

1. The isolated human NGC-407 cell line deposited under the Budapest Treaty with Deutsche Sammlung von Mkroorganismen and Zellkulturen, on 31 Mar., 2005, under accession number DSM ACC2718 or an isolated cell line obtainable therefrom.

2. The isolated cell line of claim 1, being a polyclonal cell line.

3. The isolated cell line of claim 1, being a monoclonal cell line.

4. The isolated cell line of claim 1, being transfected or transduced with an expression construct capable of directing the expression of a heterologous therapeutic gene.

5. The isolated cell line of claim 4, wherein the heterologous gene encodes a therapeutic polypeptide.

6. The isolated cell line of claim 4, wherein the heterologous gene comprises a suicide gene.

7. The isolated cell line of claim 6, wherein the suicide gene encodes a polypeptide selected from the group consisting of:
   a. a deoxyribonucleoside kinase having the amino acid sequence of any of SEQ ID No 1 to 17;
   b. a polypeptide comprising an amino acid sequence having at least 95% sequence identity to any of SEQ ID No 1, 4, 6, 7, or 17, wherein the amino acid sequence has deoxyribonucleoside kinase activity; and
   c. a polypeptide comprising an amino acid sequence having at least 90% sequence identity to any of SEQ ID No 2, 3, 5, 8, or one of 9-16, wherein the amino acid sequence has deoxyribonucleoside kinase activity.

8. The isolated cell line of claim 7, wherein the suicide gene encodes a polypeptide selected from the group consisting of:
   a. a deoxyribonucleoside kinase having the amino acid sequence of any of SEQ ID No 1 to 5;
   b. a polypeptide comprising an amino acid sequence having at least 95% sequence identity to SEQ ID No 1 or 4, wherein the amino acid sequence has deoxyribonucleoside kinase activity; and
   c. a polypeptide comprising an amino acid sequence having at least 90% sequence identity to any of SEQ ID No 2, 3, or 5, wherein the amino acid sequence has deoxyribonucleoside kinase activity.

9. The isolated cell line of claim 4, wherein the heterologous therapeutic gene encodes a neurotrophic factor.

10. The isolated cell line of claim 2, in which the heterologous therapeutic gene is encoding a neuronal survival factor.

11. The isolated cell line of claim 2, in which the heterologous therapeutic gene is encoding a nerve growth factor.

12. The isolated cell line of claim 2, in which the heterologous therapeutic gene is encoding a biologically active molecule that participates in the synthesis of a neurotransmitter substance.

13. The isolated cell line of claim 12, in which the neurotransmitter substance is acetylcholine, noradrenaline, adrenaline, 3,4-dihydroxyphenylalanine (L-DOPA), dopamine, octopamine, glutmate, aspartate, glycine, proline, χ-aminobutyric acid (GABA), tyrosine, taurine, alamine, cystathione, histamine, serotonine (5-hydroxytryptamine), substance P, Neuropeptid Y (NPY), Cholecystokinin, neurotensin, enkephalins, or somatostatin.

14. The isolated cell line of claim 2, in which the heterologous therapeutic gene is encoding a receptor.

15. The isolated cell line of claim 6, in which the suicide gene is a thymidine kinase (TK) gene.

16. The isolated cell line of claim 1, being capable of differentiating into astrocytes.

17. The cell line of claim 1, being capable of differentiating into neurons, such as dopaminergic neurons.

18. The cell line of claim 1, being capable of differentiating into glia.

19. The isolated cell line of claim 1, being capable of growing as an adherent culture.

20. The isolated cell line of claim 9, wherein the neurotrophic factor is a Nerve Growth Factor (NGF), an Insulin-like Growth Factor (IGF), a member of the Transforming Growth Factor (TGF) superfamily, Neurturin (NTN), Persephin (PSP); a Glial cell-line Derived Neurotrophic Factor (GDNF); Neublastin (NBN); a Ciliary Neurotrophic Factor (CNTF); a Brain Derived Neurotrophic Factor (BDNF); a Neurotrophin (NT), or a Tumor Necrosis Factor (TNF).

21. The cell line of claim 10, in which the neuronal survival factor is a Super Oxide Dismutase (SOD) or a Hedgehog.

22. The cell line of claim 11, in which the nerve growth factor is a Fibroblast Growth Factor (FGF), an Endothelial Growth Factor (EGF), an interferon, or an interleukin (IL).

23. The cell line of claim 12, in which the biologically active molecule that participates in the synthesis of a neurotransmitter substance is a choline acetyl transferase; a Tyrosine Hydroxylase (TH); a tyrosine decarboxylase; a thymidine kinase, a cytosine deamidase, a monoamine oxidase, a L-DOPA decarboxylase, a histidine decarboxylase, a glutamate decarboxylase, or an Ornithine Transcarbamylase (OTC).

24. The cell line of claim 14, in which the receptor binds acetylcholine, noradrenaline, adrenaline, 3,4-dihydroxyphenylalanine (L-DOPA), dopamine, octopamine, glutamate, aspartate, glycine, proline, .chi.-aminobutyric acid (GABA), tyrosine, taurine, alanine, cystathione, histamine, serotonine (5-hydroxytryptamine), substance P, Neuropeptid Y (NPY), Cholecystokinin, neurotensin, enkephalins, or somatostatin.

25. The cell line of claim 15, in which thymidine kinase (TK) gene is Herpes Simplex Virus thymidine kinase gene, the cytomegalovirus thymidine kinase gene, the varicella-zoster virus thymidine kinase gene the Gpt gene, or the cytosine deaminase gene.

26. The isolated cell line of claim 17, being capable of differentiating into dopaminergic neurons.

* * * * *

SEQUENCE LISTING

```
<160> NUMBER OF SEQ ID NOS: 21

<210> SEQ ID NO 1
<211> LENGTH: 376
<212> TYPE: PRT
<213> ORGANISM: herpes simplex virus 7

<400> SEQUENCE: 1

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
```

```
                275                 280                 285
Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 2
<211> LENGTH: 250
<212> TYPE: PRT
<213> ORGANISM: Drosophila melanogaster

<400> SEQUENCE: 2

Met Ala Glu Ala Ala Ser Cys Ala Arg Lys Gly Thr Lys Tyr Ala Glu
1               5                   10                  15

Gly Thr Gln Pro Phe Thr Val Leu Ile Glu Gly Asn Ile Gly Ser Gly
            20                  25                  30

Lys Thr Thr Tyr Leu Asn His Phe Glu Lys Tyr Lys Asn Asp Ile Cys
        35                  40                  45

Leu Leu Thr Glu Pro Val Glu Lys Trp Arg Asn Val Asn Gly Val Asn
    50                  55                  60

Leu Leu Glu Leu Met Tyr Lys Asp Pro Lys Lys Trp Ala Met Pro Phe
65                  70                  75                  80

Gln Ser Tyr Val Thr Leu Thr Met Leu Gln Ser His Thr Ala Pro Thr
                85                  90                  95

Asn Lys Lys Leu Lys Ile Met Glu Arg Ser Ile Phe Ser Ala Arg Tyr
            100                 105                 110

Cys Phe Val Glu Asn Met Arg Arg Asn Gly Ser Leu Glu Gln Gly Met
        115                 120                 125

Tyr Asn Thr Leu Glu Glu Trp Tyr Lys Phe Ile Glu Glu Ser Ile His
    130                 135                 140

Val Gln Ala Asp Leu Ile Ile Tyr Leu Arg Thr Ser Pro Glu Val Ala
145                 150                 155                 160

Tyr Glu Arg Ile Arg Gln Arg Ala Arg Ser Glu Glu Ser Cys Val Pro
                165                 170                 175

Leu Lys Tyr Leu Gln Glu Leu His Glu Leu His Glu Asp Trp Leu Ile
            180                 185                 190

His Gln Arg Arg Pro Gln Ser Cys Lys Val Leu Val Leu Asp Ala Asp
        195                 200                 205

Leu Asn Leu Glu Asn Ile Gly Thr Glu Tyr Gln Arg Ser Glu Ser Ser
    210                 215                 220

Ile Phe Asp Ala Ile Ser Ser Asn Gln Gln Pro Ser Pro Val Leu Val
225                 230                 235                 240

Ser Pro Ser Lys Arg Gln Arg Val Ala Arg
                245                 250

<210> SEQ ID NO 3
<211> LENGTH: 234
<212> TYPE: PRT
```

<213> ORGANISM: Lycopersicon esculentum

<400> SEQUENCE: 3

```
Met Ala Phe Ser Ser Ser Ala Arg Asn Pro Val Asp Leu Arg Asn Gly
1               5                   10                  15

Ser Lys Asn Ser Phe Cys Pro Val Gly Glu Ile His Val Ile Val Gly
            20                  25                  30

Pro Met Phe Ala Gly Lys Thr Thr Ala Leu Leu Arg Arg Val Asn Leu
        35                  40                  45

Glu Ser Asn Asp Gly Arg Asn Val Val Leu Ile Lys Ser Ser Lys Asp
    50                  55                  60

Ala Arg Tyr Ala Val Asp Ala Val Val Thr His Asp Gly Thr Arg Phe
65                  70                  75                  80

Pro Cys Trp Ser Leu Pro Asp Leu Ser Ser Phe Lys Gln Arg Phe Gly
                85                  90                  95

Lys Asp Ala Tyr Glu Lys Val Asp Val Ile Gly Ile Asp Glu Ala Gln
            100                 105                 110

Phe Phe Gly Asp Leu Tyr Glu Phe Cys Cys Asn Ala Ala Asp Phe Asp
        115                 120                 125

Gly Lys Ile Ile Val Val Ala Gly Leu Asp Gly Asp Tyr Leu Arg Lys
130                 135                 140

Ser Phe Gly Ser Val Leu Asp Ile Ile Pro Leu Ala Asp Thr Val Thr
145                 150                 155                 160

Lys Leu Thr Ala Arg Cys Glu Leu Cys Asn Arg Arg Ala Phe Phe Thr
                165                 170                 175

Phe Arg Lys Thr Asn Glu Thr Glu Thr Glu Leu Ile Gly Gly Ala Asp
            180                 185                 190

Ile Tyr Met Pro Val Cys Arg Gln His Tyr Val Asn Gly Gln Ser Val
        195                 200                 205

Asn Glu Ser Ala Lys Met Val Leu Gly Ser His Lys Val Ser Asn Glu
    210                 215                 220

Leu Ile Leu Glu Ser Pro Leu Val Asp Pro
225                 230
```

<210> SEQ ID NO 4
<211> LENGTH: 361
<212> TYPE: PRT
<213> ORGANISM: Arabidopsis thaliana

<400> SEQUENCE: 4

```
Met Val Asp Tyr Leu Arg Ser Ser Val Gly Ile Ile His Arg Asn His
1               5                   10                  15

Ala Glu Ser Ile Thr Thr Phe Ile Lys Glu Ser Val Asp Glu Leu
            20                  25                  30

Lys Asp Ser Gly Pro Glu Pro Asn Leu Asn Val Lys Lys Arg Leu Thr
        35                  40                  45

Phe Cys Val Glu Gly Asn Ile Ser Val Gly Lys Ser Thr Phe Leu Gln
    50                  55                  60

Arg Ile Ala Asn Glu Thr Val Glu Leu Gln Asp Leu Val Glu Ile Val
65                  70                  75                  80

Pro Glu Pro Val Asp Lys Trp Gln Asp Val Gly Pro Asp His Phe Asn
                85                  90                  95

Ile Leu Asp Ala Phe Tyr Ser Glu Pro Gln Arg Tyr Ala Tyr Thr Phe
            100                 105                 110

Gln Asn Tyr Val Phe Val Thr Arg Leu Met Gln Glu Lys Glu Ser Ala
        115                 120                 125
```

Ser Gly Val Lys Pro Leu Arg Leu Met Glu Arg Ser Val Phe Ser Asp
    130                 135                 140

Arg Met Val Phe Val Arg Ala Val His Glu Ala Lys Trp Met Asn Glu
145                 150                 155                 160

Met Glu Ile Ser Ile Tyr Asp Ser Trp Phe Asp Pro Val Val Ser Ser
                165                 170                 175

Leu Pro Gly Leu Val Pro Asp Gly Phe Ile Tyr Leu Arg Ala Ser Pro
            180                 185                 190

Asp Thr Cys His Lys Arg Met Met Leu Arg Lys Arg Ala Glu Glu Gly
        195                 200                 205

Gly Val Ser Leu Lys Tyr Leu Gln Asp Leu His Glu Lys His Glu Ser
    210                 215                 220

Trp Leu Leu Pro Phe Glu Ser Gly Asn His Gly Val Leu Ser Val Ser
225                 230                 235                 240

Arg Pro Ser Leu His Met Asp Asn Ser Leu His Pro Asp Ile Lys Asp
                245                 250                 255

Arg Val Phe Tyr Leu Glu Gly Asn His Met His Ser Ser Ile Gln Lys
            260                 265                 270

Val Pro Ala Leu Val Leu Asp Cys Glu Pro Asn Ile Asp Phe Ser Arg
        275                 280                 285

Asp Ile Glu Ala Lys Thr Gln Tyr Ala Arg Gln Val Ala Glu Phe Phe
    290                 295                 300

Glu Phe Val Lys Lys Lys Gln Glu Thr Ser Thr Glu Lys Ser Asn Ser
305                 310                 315                 320

Gln Ser Pro Val Leu Leu Pro His Gln Asn Gly Gly Leu Trp Met Gly
                325                 330                 335

Pro Ala Gly Asn His Val Pro Gly Leu Asp Leu Pro Pro Leu Asp Leu
            340                 345                 350

Lys Ser Leu Leu Thr Arg Pro Ser Ala
        355                 360

<210> SEQ ID NO 5
<211> LENGTH: 250
<212> TYPE: PRT
<213> ORGANISM: Drosophila melanogaster

<400> SEQUENCE: 5

Met Ala Glu Ala Ala Ser Cys Ala Arg Lys Gly Thr Lys Tyr Ala Glu
1               5                   10                  15

Gly Thr Gln Pro Phe Thr Val Leu Ile Glu Gly Asn Ile Gly Ser Gly
            20                  25                  30

Lys Thr Thr Tyr Leu Asn His Phe Glu Lys Tyr Lys Asn Asp Ile Cys
        35                  40                  45

Leu Leu Thr Glu Pro Val Glu Lys Trp Arg Asn Val Asn Gly Val Asn
50                  55                  60

Leu Leu Glu Leu Met Tyr Lys Asp Pro Lys Lys Trp Ala Met Pro Phe
65                  70                  75                  80

Gln Ser Tyr Ala Thr Leu Thr Met Leu Gln Ser His Thr Ala Pro Thr
                85                  90                  95

Asn Lys Lys Leu Lys Ile Met Glu Arg Ser Ile Phe Ser Ala Arg Tyr
            100                 105                 110

Cys Phe Val Glu Asn Met Arg Arg Asn Gly Ser Leu Glu Gln Gly Met
        115                 120                 125

Tyr Asn Thr Leu Glu Glu Trp Tyr Lys Phe Ile Glu Glu Ser Ile His
    130                 135                 140

```
Val Gln Ala Asp Leu Ile Ile Tyr Leu Arg Thr Ser Pro Glu Val Ala
145                 150                 155                 160

Tyr Glu Arg Ile Arg Gln Arg Ala Arg Ser Glu Ser Cys Val Pro
            165                 170                 175

Leu Lys Tyr Leu Gln Glu Leu His Glu Leu His Glu Asp Trp Leu Ile
        180                 185                 190

His Gln Arg Arg Pro Gln Ser Cys Lys Val Leu Val Leu Asp Ala Asp
        195                 200                 205

Leu Asp Leu Glu Asn Ile Gly Thr Glu Tyr Gln Arg Ser Glu Ser Ser
    210                 215                 220

Ile Phe Asp Ala Ile Ser Ser Asn Gln Gln Pro Ser Pro Val Pro Val
225                 230                 235                 240

Ser Pro Ser Lys Arg Gln Arg Val Ala Arg
                245                 250

<210> SEQ ID NO 6
<211> LENGTH: 580
<212> TYPE: PRT
<213> ORGANISM: Arabidopsis thaliana

<400> SEQUENCE: 6

Met Gln Lys Ile Leu Cys Lys Ser Thr Thr Ser Ser Thr Pro Val Leu
1               5                   10                  15

Ser Thr Pro Val Asn Ser Leu Ala Ala Gly Phe Ile Ser Leu Gly Phe
            20                  25                  30

Lys Thr Pro Val Lys Asn Leu Pro Pro Cys Ser Thr Thr Lys Pro Leu
        35                  40                  45

Ser Thr Cys Phe Phe Ser Thr Ser Ala Met Pro Thr Thr Thr Ala Ser
    50                  55                  60

Val Ser Ser Gly Gly Val Gly Phe Ser Ala Tyr Leu Gln Arg Thr Val
65                  70                  75                  80

His Lys Pro Ala Pro Ala Ser Val Arg Phe Ser Thr Ala Gly Tyr Arg
                85                  90                  95

Thr Cys Arg Cys Ser Ile Asp Gly Thr Asn Arg Ala Trp Val Gly Arg
            100                 105                 110

Thr Gly Ser Trp Arg Ala Leu Phe Cys Ser Asp Ser Thr Gly Gly Leu
        115                 120                 125

Thr Pro Val Asn Ala Thr Ala Gly Ala Val Val Glu Ser Glu Glu Glu
    130                 135                 140

Ser Asp Gly Glu Asp Glu Asp Glu Glu Lys Asp Glu Lys Pro Val Arg
145                 150                 155                 160

Met Asn Arg Arg Asn Arg Ser Ser Ser Gly Ser Gly Glu Phe Val Gly
                165                 170                 175

Asn Pro Asp Leu Leu Lys Ile Pro Gly Val Gly Leu Arg Asn Gln Arg
            180                 185                 190

Lys Leu Val Asp Asn Gly Ile Gly Asp Val Ala Glu Leu Lys Lys Leu
        195                 200                 205

Tyr Lys Asp Lys Phe Trp Lys Ala Ser Gln Lys Met Val Asp Tyr Leu
    210                 215                 220

Arg Ser Ser Val Gly Ile Ile His Arg Asn His Ala Glu Ser Ile Thr
225                 230                 235                 240

Thr Phe Ile Lys Glu Ser Val Asp Asp Glu Leu Lys Asp Ser Gly Pro
                245                 250                 255

Glu Pro Asn Leu Asn Val Lys Lys Arg Leu Thr Phe Cys Val Glu Gly
            260                 265                 270
```

Asn Ile Ser Val Gly Lys Ser Thr Phe Leu Gln Arg Ile Ala Asn Glu
            275                 280                 285

Thr Val Glu Leu Gln Asp Leu Val Glu Ile Val Pro Glu Pro Val Asp
        290                 295                 300

Lys Trp Gln Asp Val Gly Pro Asp His Phe Asn Ile Leu Asp Ala Phe
305                 310                 315                 320

Tyr Ser Glu Pro Gln Arg Tyr Ala Tyr Thr Phe Gln Asn Tyr Val Phe
                325                 330                 335

Val Thr Arg Leu Met Gln Glu Lys Glu Ser Ala Ser Gly Val Lys Pro
            340                 345                 350

Leu Arg Leu Met Glu Arg Ser Val Phe Ser Asp Arg Met Val Phe Val
        355                 360                 365

Arg Ala Val His Glu Ala Lys Trp Met Asn Glu Met Glu Ile Ser Ile
    370                 375                 380

Tyr Asp Ser Trp Phe Asp Pro Val Val Ser Ser Leu Pro Gly Leu Val
385                 390                 395                 400

Pro Asp Gly Phe Ile Tyr Leu Arg Ala Ser Pro Asp Thr Cys His Lys
                405                 410                 415

Arg Met Met Leu Arg Lys Arg Ala Glu Gly Gly Val Ser Leu Lys
            420                 425                 430

Tyr Leu Gln Asp Leu His Glu Lys His Glu Ser Trp Leu Leu Pro Phe
        435                 440                 445

Glu Ser Gly Asn His Gly Val Leu Ser Val Ser Arg Pro Ser Leu His
    450                 455                 460

Met Asp Asn Ser Leu His Pro Asp Ile Lys Asp Arg Val Phe Tyr Leu
465                 470                 475                 480

Glu Gly Asn His Met His Ser Ser Ile Gln Lys Val Pro Ala Leu Val
                485                 490                 495

Leu Asp Cys Glu Pro Asn Ile Asp Phe Ser Arg Asp Ile Glu Ala Lys
            500                 505                 510

Thr Gln Tyr Ala Arg Gln Val Ala Glu Phe Phe Glu Phe Val Lys Lys
        515                 520                 525

Lys Gln Glu Thr Ser Thr Glu Lys Ser Asn Ser Gln Ser Pro Val Leu
    530                 535                 540

Leu Pro His Gln Asn Gly Gly Leu Trp Met Gly Pro Ala Gly Asn His
545                 550                 555                 560

Val Pro Gly Leu Asp Leu Pro Pro Leu Asp Leu Lys Ser Leu Leu Thr
                565                 570                 575

Arg Pro Ser Ala
            580

<210> SEQ ID NO 7
<211> LENGTH: 300
<212> TYPE: PRT
<213> ORGANISM: Oryza sativa

<400> SEQUENCE: 7

Met Val Glu Phe Leu Gln Ser Ser Val Gly Ile Ile His Lys Asn His
1               5                   10                  15

Ala Glu Ser Ile Thr Leu Phe Ile Lys Glu Ser Val Asp Glu Glu Leu
            20                  25                  30

Lys Gly Thr Asp Ser Pro Asn Val Ser Lys Asn Lys Arg Leu Thr Phe
        35                  40                  45

Cys Val Glu Gly Asn Ile Ser Val Gly Lys Thr Thr Phe Leu Gln Arg
    50                  55                  60

```
Ile Ala Asn Glu Thr Ile Glu Leu Arg Asp Leu Val Glu Ile Val Pro
 65                  70                  75                  80

Glu Pro Ile Ala Lys Trp Gln Asp Val Gly Pro Asp His Phe Asn Ile
                 85                  90                  95

Leu Asp Ala Phe Tyr Ala Glu Pro Gln Arg Tyr Ala Tyr Thr Phe Gln
                100                 105                 110

Asn Tyr Val Phe Val Thr Arg Val Met Gln Glu Lys Glu Ser Ser Ser
                115                 120                 125

Gly Ile Lys Pro Leu Arg Leu Met Glu Arg Ser Val Phe Ser Asp Arg
                130                 135                 140

Met Val Val Lys Phe Leu Lys Val Phe Val Arg Ala Val His Glu Ala
145                 150                 155                 160

Asn Trp Met Asn Glu Met Glu Ile Ser Ile Tyr Asp Ser Trp Phe Asp
                165                 170                 175

Pro Val Val Ser Ser Leu Pro Gly Leu Ile Pro Asp Gly Phe Ile Tyr
                180                 185                 190

Leu Arg Ala Ser Pro Asp Thr Cys His Lys Arg Met Met Val Arg Lys
                195                 200                 205

Arg Ser Glu Glu Gly Gly Val Thr Leu Asp Tyr Leu Arg Gly Leu His
                210                 215                 220

Glu Lys His Glu Ser Trp Leu Leu Pro Ser Lys Gly Gln Gly Pro Gly
225                 230                 235                 240

Val Leu Ser Val Ser Gln Val Pro Val His Met Glu Gly Ser Leu Pro
                245                 250                 255

Pro Asp Ile Arg Glu Arg Val Phe Tyr Leu Glu Gly Asp His Met His
                260                 265                 270

Ser Ser Ile Gln Lys Val Pro Ala Leu Val Leu Asp Cys Glu His Asp
                275                 280                 285

Ile Asp Phe Asn Lys Asp Ile Glu Ala Lys Arg Gln
                290                 295                 300

<210> SEQ ID NO 8
<211> LENGTH: 260
<212> TYPE: PRT
<213> ORGANISM: Homo sapiens

<400> SEQUENCE: 8

Met Ala Thr Pro Pro Lys Arg Ser Cys Pro Ser Phe Ser Ala Ser Ser
  1               5                  10                  15

Glu Gly Thr Arg Ile Lys Lys Ile Ser Ile Gly Asn Ile Ala Ala
                 20                  25                  30

Gly Lys Ser Thr Phe Val Asn Ile Leu Lys Gln Leu Cys Glu Asp Trp
                 35                  40                  45

Glu Val Val Pro Glu Pro Val Ala Arg Trp Cys Asn Val Gln Ser Thr
 50                  55                  60

Gln Asp Glu Phe Glu Glu Leu Thr Met Ser Gln Lys Asn Gly Gly Asn
 65                  70                  75                  80

Val Leu Gln Met Met Tyr Glu Lys Pro Glu Arg Trp Ser Phe Thr Phe
                 85                  90                  95

Gln Thr Tyr Ala Cys Leu Ser Arg Ile Arg Ala Gln Leu Ala Ser Leu
                100                 105                 110

Asn Gly Lys Leu Lys Asp Ala Glu Lys Pro Val Leu Phe Phe Glu Arg
                115                 120                 125

Ser Val Tyr Ser Asp Arg Tyr Ile Phe Ala Ser Asn Leu Tyr Glu Ser
                130                 135                 140
```

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Lys Val Lys Glu Phe
                245                 250                 255

Leu Ser Thr Leu
            260

<210> SEQ ID NO 9
<211> LENGTH: 277
<212> TYPE: PRT
<213> ORGANISM: Homo sapiens

<400> SEQUENCE: 9

Met Ala Ala Gly Arg Leu Phe Leu Ser Arg Leu Arg Ala Pro Phe Ser
1               5                   10                  15

Ser Met Ala Lys Ser Pro Leu Glu Gly Val Ser Ser Arg Gly Leu
            20                  25                  30

His Ala Gly Arg Gly Pro Arg Arg Leu Ser Ile Glu Gly Asn Ile Ala
            35                  40                  45

Val Gly Lys Ser Thr Phe Val Lys Leu Leu Thr Lys Thr Tyr Pro Glu
        50                  55                  60

Trp His Val Ala Thr Glu Pro Val Ala Thr Trp Gln Asn Ile Gln Ala
65              70                  75                  80

Ala Gly Asn Gln Lys Ala Cys Thr Ala Gln Ser Leu Gly Asn Leu Leu
                85                  90                  95

Asp Met Met Tyr Arg Glu Pro Ala Arg Trp Ser Tyr Thr Phe Gln Thr
            100                 105                 110

Phe Ser Phe Leu Ser Arg Leu Lys Val Gln Leu Glu Pro Phe Pro Glu
        115                 120                 125

Lys Leu Leu Gln Ala Arg Lys Pro Val Gln Ile Phe Glu Arg Ser Val
130                 135                 140

Tyr Ser Asp Arg Tyr Ile Phe Ala Lys Asn Leu Phe Glu Asn Gly Ser
145                 150                 155                 160

Leu Ser Asp Ile Glu Trp His Ile Tyr Gln Asp Trp His Ser Phe Leu
                165                 170                 175

Leu Trp Glu Phe Ala Ser Arg Ile Thr Leu His Gly Phe Ile Tyr Leu
            180                 185                 190

Gln Ala Ser Pro Gln Val Cys Leu Lys Arg Leu Tyr Gln Arg Ala Arg
        195                 200                 205

Glu Glu Glu Lys Gly Ile Glu Leu Ala Tyr Leu Glu Gln Leu His Gly
    210                 215                 220

Gln His Glu Ala Trp Leu Ile His Lys Thr Thr Lys Leu His Phe Glu
225                 230                 235                 240

Ala Leu Met Asn Ile Pro Val Leu Val Leu Asp Val Asn Asp Asp Phe
                245                 250                 255

Ser Glu Glu Val Thr Lys Gln Glu Asp Leu Met Arg Glu Val Asn Thr
            260                 265                 270

Phe Val Lys Asn Leu
            275

<210> SEQ ID NO 10
<211> LENGTH: 234
<212> TYPE: PRT
<213> ORGANISM: Homo sapiens

<400> SEQUENCE: 10

Met Gly Ala Phe Cys Gln Arg Pro Ser Ser Asp Lys Glu Gln Glu Lys
1               5                   10                  15

Glu Lys Lys Ser Val Ile Cys Val Glu Gly Asn Ile Ala Gly Gly Lys
            20                  25                  30

Thr Thr Cys Leu Glu Phe Phe Ser Asn Ala Thr Asp Val Glu Val Leu
        35                  40                  45

Thr Glu Pro Val Ser Lys Trp Arg Asn Val Arg Gly His Asn Pro Leu
    50                  55                  60

Gly Leu Met Tyr His Asp Ala Ser Arg Trp Gly Leu Thr Leu Gln Thr
65                  70                  75                  80

Tyr Val Gln Leu Thr Met Leu Asp Arg His Thr Arg Pro Gln Val Ser
                85                  90                  95

Ser Val Arg Leu Met Glu Arg Ser Ile His Ser Ala Arg Tyr Ile Phe
            100                 105                 110

Val Glu Asn Leu Tyr Arg Ser Gly Lys Met Pro Glu Val Asp Tyr Val
        115                 120                 125

Val Leu Ser Glu Trp Phe Asp Trp Ile Leu Arg Asn Met Asp Val Ser
    130                 135                 140

Val Asp Leu Ile Val Tyr Leu Arg Thr Asn Pro Glu Thr Cys Tyr Gln
145                 150                 155                 160

Arg Leu Lys Lys Arg Cys Arg Glu Glu Lys Val Ile Pro Leu Glu
                165                 170                 175

Tyr Leu Glu Ala Ile His His Leu His Glu Glu Trp Leu Ile Lys Gly
            180                 185                 190

Ser Leu Phe Pro Met Ala Ala Pro Val Leu Val Ile Glu Ala Asp His
        195                 200                 205

His Met Glu Arg Met Leu Glu Leu Phe Glu Gln Asn Arg Asp Arg Ile
    210                 215                 220

Leu Thr Pro Glu Asn Arg Lys His Cys Pro
225                 230

<210> SEQ ID NO 11
<211> LENGTH: 234
<212> TYPE: PRT
<213> ORGANISM: Homo sapiens

<400> SEQUENCE: 11

Met Ser Cys Ile Asn Leu Pro Thr Val Leu Pro Gly Ser Pro Ser Lys
1               5                   10                  15

Thr Arg Gly Gln Ile Gln Val Ile Leu Gly Pro Met Phe Ser Gly Lys
            20                  25                  30

Ser Thr Glu Leu Met Arg Arg Val Arg Arg Phe Gln Ile Ala Gln Tyr
        35                  40                  45

Lys Cys Leu Val Ile Lys Tyr Ala Lys Asp Thr Arg Tyr Ser Ser Ser
    50                  55                  60

```
Phe Cys Thr His Asp Arg Asn Thr Met Glu Ala Leu Pro Ala Cys Leu
 65                  70                  75                  80

Leu Arg Asp Val Ala Gln Glu Ala Leu Gly Val Ala Val Ile Gly Ile
                 85                  90                  95

Asp Glu Gly Gln Phe Phe Pro Asp Ile Met Glu Phe Cys Glu Ala Met
            100                 105                 110

Ala Asn Ala Gly Lys Thr Val Ile Val Ala Ala Leu Asp Gly Thr Phe
            115                 120                 125

Gln Arg Lys Pro Phe Gly Ala Ile Leu Asn Leu Val Pro Leu Ala Glu
130                 135                 140

Ser Val Val Lys Leu Thr Ala Val Cys Met Glu Cys Phe Arg Glu Ala
145                 150                 155                 160

Ala Tyr Thr Lys Arg Leu Gly Thr Glu Lys Glu Val Glu Val Ile Gly
                165                 170                 175

Gly Ala Asp Lys Tyr His Ser Val Cys Arg Leu Cys Tyr Phe Lys Lys
            180                 185                 190

Ala Ser Gly Gln Pro Ala Gly Pro Asp Asn Lys Glu Asn Cys Pro Val
            195                 200                 205

Pro Gly Lys Pro Gly Glu Ala Val Ala Ala Arg Lys Leu Phe Ala Pro
210                 215                 220

Gln Gln Ile Leu Gln Cys Ser Pro Ala Asn
225                 230
```

<210> SEQ ID NO 12
<211> LENGTH: 248
<212> TYPE: PRT
<213> ORGANISM: Bombyx mori
<400> SEQUENCE: 12

```
Met Ser Ala Asn Asn Val Lys Pro Phe Thr Val Phe Val Glu Gly Asn
  1               5                  10                  15

Ile Gly Ser Gly Lys Thr Thr Phe Leu Glu His Phe Arg Gln Phe Glu
                 20                  25                  30

Asp Ile Thr Leu Leu Thr Glu Pro Val Glu Met Trp Arg Asp Leu Lys
             35                  40                  45

Gly Cys Asn Leu Leu Glu Leu Met Tyr Lys Asp Pro Glu Lys Trp Ala
 50                  55                  60

Met Thr Phe Gln Ser Tyr Val Ser Leu Thr Met Leu Asp Met His Arg
 65                  70                  75                  80

Arg Pro Ala Pro Thr Pro Val Lys Leu Met Glu Arg Ser Leu Phe Ser
                 85                  90                  95

Ala Arg Tyr Cys Phe Val Glu His Ile Met Arg Asn Asn Thr Leu His
            100                 105                 110

Pro Ala Gln Phe Ala Val Leu Asp Glu Trp Phe Arg Phe Ile Gln His
            115                 120                 125

Asn Ile Pro Ile Asp Ala Asp Leu Ile Val Tyr Leu Lys Thr Ser Pro
130                 135                 140

Ser Ile Val Tyr Gln Arg Ile Lys Lys Arg Ala Arg Ser Glu Glu Gln
145                 150                 155                 160

Cys Val Pro Leu Ser Tyr Ile Glu Glu Leu His Arg Leu His Glu Asp
                165                 170                 175

Trp Leu Ile Asn Arg Ile His Ala Glu Cys Pro Ala Pro Val Leu Val
            180                 185                 190

Leu Asp Ala Asp Leu Asp Leu Ser Gln Ile Thr Asp Gly Tyr Lys Arg
            195                 200                 205
```

```
Ser Glu His Gln Ile Leu Arg Lys Ala Val Asn Val Met Ser Ser
    210                 215                 220

Pro Asn Lys His Ser Pro Lys Lys Pro Ile Ser Thr Thr Pro Ile Lys
225                 230                 235                 240

Ile Thr Pro His Met Arg Ile Leu
                245

<210> SEQ ID NO 13
<211> LENGTH: 246
<212> TYPE: PRT
<213> ORGANISM: Anopheles gambiae

<400> SEQUENCE: 13

Met Pro Pro Ile Ala Ser Glu Lys Leu Gly Ala Ser Gly Lys Lys Pro
1               5                   10                  15

Phe Thr Val Phe Val Glu Gly Asn Ile Gly Ser Gly Lys Thr Thr Phe
                20                  25                  30

Leu Asn His Phe Gln Lys Phe Asn Asp Ile Cys Leu Leu Thr Glu Pro
            35                  40                  45

Val Glu Lys Trp Arg Asn Cys Gly Gly Val Asn Leu Leu Asp Leu Met
        50                  55                  60

Tyr Lys Glu Ser His Arg Trp Ala Met Pro Phe Gln Thr Tyr Val Thr
65                  70                  75                  80

Leu Thr Met Leu Asp Met His Thr Cys Gln Thr Asp Lys Ser Val Lys
                85                  90                  95

Leu Met Glu Arg Ser Leu Phe Ser Ala Arg Asn Cys Phe Val Glu Ser
            100                 105                 110

Met Leu Ala Ser Gly Ser Leu His Gln Gly Met Tyr Asn Val Leu Gln
        115                 120                 125

Glu Trp Tyr Asp Phe Ile Cys Cys Asn Ile His Ile Gln Ala Asp Leu
130                 135                 140

Ile Val Tyr Leu Gln Thr Ser Pro Glu Val Val Tyr Glu Arg Met Lys
145                 150                 155                 160

Gln Arg Ala Arg Ser Glu Glu Ser Cys Val Pro Leu Glu Tyr Leu Lys
                165                 170                 175

Glu Leu His Glu Leu His Glu Asn Trp Leu Ile His Gly Ala Ser Pro
            180                 185                 190

Arg Pro Ala Pro Val Leu Val Leu Asn Ala Asp Leu Asp Leu Asn Thr
        195                 200                 205

Ile Gly Ala Glu Tyr Gly Arg Ser Glu Thr Ser Ile Leu Lys Pro Ile
210                 215                 220

Leu Ile Glu Asn Thr Asn Gln His Ala Ile Leu Thr Ser Pro Ala Lys
225                 230                 235                 240

Arg Ala Lys Thr Asp Phe
                245

<210> SEQ ID NO 14
<211> LENGTH: 276
<212> TYPE: PRT
<213> ORGANISM: Oryza sativa

<400> SEQUENCE: 14

Met Ser Ser Ile Cys Ala Met Arg Ser Leu Leu Ala Ala Ser Thr Phe
1               5                   10                  15

Leu Arg Ser Gly Ala Ser Pro Leu Leu Arg Pro Leu Ser Arg Pro Leu
                20                  25                  30

Pro Ser Arg Leu Asn Leu Ser Arg Phe Gly Pro Val Arg Pro Val Ser
```

```
                35                  40                  45
Ala Ala Ala Ala Ala Asp Lys Ser Arg Gly Gly Gly Ser Ala
    50                  55                  60

Met Glu Ala Gln Pro Ser Tyr Pro Gly Glu Ile His Val Ile Val Gly
 65                  70                  75                  80

Pro Met Phe Ala Gly Lys Thr Thr Ala Leu Leu Arg Arg Val Gln Val
                 85                  90                  95

Glu Ala Gly Thr Gly Arg Asn Val Ala Leu Ile Lys Ser Asp Lys Asp
            100                 105                 110

Asn Arg Tyr Gly Leu Asp Ser Val Val Thr His Asp Gly Thr Lys Met
        115                 120                 125

Pro Cys Trp Ala Leu Pro Glu Leu Ser Ser Phe Gln Asp Lys Leu Gly
    130                 135                 140

Thr Glu Ala Tyr Asp Lys Val Asp Val Ile Gly Ile Asp Glu Ala Gln
145                 150                 155                 160

Phe Phe Asp Asp Leu His Asp Phe Cys Cys Lys Ala Ala Asp Arg Asp
                165                 170                 175

Gly Lys Ile Val Val Val Ala Gly Leu Asp Gly Asp Tyr Lys Arg Asn
            180                 185                 190

Lys Phe Gly Ser Val Leu Asp Ile Ile Pro Leu Ala Asp Ser Val Thr
        195                 200                 205

Lys Leu Thr Ala Arg Cys Glu Leu Cys Gly Arg Arg Ala Phe Phe Thr
    210                 215                 220

Leu Arg Lys Thr Arg Glu Thr Lys Thr Glu Leu Ile Gly Gly Ala Asp
225                 230                 235                 240

Val Tyr Met Pro Val Cys Arg Gln His Tyr Leu Asp Gly Gln Ile Val
                245                 250                 255

Ile Glu Ala Thr Arg Ile Val Leu Asp Leu Glu Lys Ser Lys Val Ile
            260                 265                 270

His Ala Phe Lys
        275

<210> SEQ ID NO 15
<211> LENGTH: 238
<212> TYPE: PRT
<213> ORGANISM: Arabidopsis thaliana

<400> SEQUENCE: 15

Met Ala Thr Leu Lys Ala Ser Phe Leu Ile Lys Thr Leu Asp Ser Asp
 1               5                  10                  15

Val Thr Gly Asp Phe Leu Ser Asp Leu Glu Arg Arg Gly Ser Gly Ala
                 20                  25                  30

Val His Val Ile Met Gly Pro Met Phe Ser Gly Lys Ser Thr Ser Leu
            35                  40                  45

Leu Arg Arg Ile Lys Ser Glu Ile Ser Asp Gly Arg Ser Val Ala Met
        50                  55                  60

Leu Lys Ser Ser Lys Asp Thr Arg Tyr Ala Lys Asp Ser Val Val Thr
 65                  70                  75                  80

His Asp Gly Ile Gly Phe Pro Cys Trp Ala Leu Pro Asp Leu Met Ser
                 85                  90                  95

Phe Pro Glu Lys Phe Gly Leu Asp Ala Tyr Asn Lys Leu Asp Val Ile
            100                 105                 110

Gly Ile Asp Glu Ala Gln Phe Phe Gly Asp Leu Tyr Glu Phe Cys Cys
        115                 120                 125

Lys Val Ala Asp Asp Asp Gly Lys Ile Val Ile Val Ala Gly Leu Asp
```

```
                130                 135                 140
Gly Asp Tyr Leu Arg Arg Ser Phe Gly Ala Val Leu Asp Ile Ile Pro
145                 150                 155                 160

Ile Ala Asp Ser Val Thr Lys Leu Thr Ala Arg Cys Glu Val Cys Gly
                165                 170                 175

His Lys Ala Phe Phe Thr Leu Arg Lys Asn Cys Asp Thr Arg Thr Glu
                180                 185                 190

Leu Ile Gly Gly Ala Asp Val Tyr Met Pro Val Cys Arg Lys His Tyr
                195                 200                 205

Ile Thr Asn His Ile Val Ile Lys Ala Ser Lys Lys Val Leu Glu Asp
                210                 215                 220

Ser Asp Lys Ala Arg Ala Glu Ser Cys Val Ala Ala Thr Ile
225                 230                 235

<210> SEQ ID NO 16
<211> LENGTH: 277
<212> TYPE: PRT
<213> ORGANISM: Arabidopsis thaliana

<400> SEQUENCE: 16

Met Arg Thr Leu Ile Ser Pro Ser Leu Ala Pro Phe Ser Leu His Leu
1                   5                   10                  15

His Lys Pro Ser Leu Phe Ser Thr Ala Leu Arg Phe Ser Phe Ser Ile
                20                  25                  30

Asn Asn Ile Thr Pro Thr Asn Ser Pro Pro Ser Thr Ile Ser Thr Arg
                35                  40                  45

Lys Leu Gln Thr Lys Ala Thr Arg Val Thr Ser Ser Ser Ser Ser Gln
50                  55                  60

Pro Leu Ser Ser Ser Pro Gly Glu Ile His Val Val Val Gly Pro
65                  70                  75                  80

Met Phe Ser Gly Lys Thr Thr Thr Leu Leu Arg Arg Ile Leu Ala Glu
                85                  90                  95

Arg Glu Thr Gly Lys Arg Ile Ala Ile Ile Lys Ser Asn Lys Asp Thr
                100                 105                 110

Arg Tyr Cys Thr Glu Ser Ile Val Thr His Asp Gly Glu Lys Tyr Pro
                115                 120                 125

Cys Trp Ser Leu Pro Asp Leu Ser Ser Phe Lys Glu Arg Phe Gly Phe
                130                 135                 140

Asp Asp Tyr Glu Asn Arg Leu Asp Val Ile Gly Ile Asp Glu Ala Gln
145                 150                 155                 160

Phe Phe Gly Asp Leu Tyr Glu Phe Cys Arg Glu Ala Ala Asp Lys Glu
                165                 170                 175

Gly Lys Thr Val Ile Val Ala Gly Leu Asp Gly Asp Phe Met Arg Arg
                180                 185                 190

Arg Phe Gly Ser Val Leu Asp Leu Ile Pro Ile Ala Asp Thr Val Thr
                195                 200                 205

Lys Leu Thr Ser Arg Cys Glu Val Cys Gly Lys Arg Ala Leu Phe Thr
                210                 215                 220

Met Arg Lys Thr Glu Glu Lys Glu Thr Glu Leu Ile Gly Gly Ala Glu
225                 230                 235                 240

Val Tyr Met Pro Val Cys Arg Ser His Tyr Val Cys Gly Gln Asn Val
                245                 250                 255

Leu Glu Thr Ala Arg Ala Val Leu Asp Ser Ser Asn Asn His Ser Val
                260                 265                 270

Val Ala Ser Ser Leu
```

275

<210> SEQ ID NO 17
<211> LENGTH: 365
<212> TYPE: PRT
<213> ORGANISM: Lycopersicon esculentum

<400> SEQUENCE: 17

```
Met Val Glu Phe Leu Gln Ser Ser Ile Gly Ile Ile His Arg Asn His
1               5                   10                  15

Ala Glu Ser Ile Thr Thr Tyr Ile Arg Lys Ser Val Asp Glu Glu Leu
            20                  25                  30

Lys Glu Asn Asn Ser Asp Ser Asn Val Lys Ser Thr Gln Lys Lys Arg
        35                  40                  45

Leu Thr Phe Cys Val Glu Gly Asn Ile Ser Val Gly Lys Thr Thr Phe
    50                  55                  60

Leu Gln Arg Ile Ala Asn Glu Thr Leu Glu Leu Gln Asp Leu Val Glu
65                  70                  75                  80

Ile Val Pro Glu Pro Ile Ala Lys Trp Gln Asp Ile Gly Pro Asp His
                85                  90                  95

Phe Asn Ile Leu Asp Ala Phe Tyr Ala Glu Pro Gln Arg Tyr Ala Tyr
            100                 105                 110

Thr Phe Gln Asn Tyr Val Phe Val Thr Arg Val Met Gln Glu Arg Glu
        115                 120                 125

Ser Ser Gly Gly Ile Arg Pro Leu Arg Leu Met Glu Arg Ser Val Phe
    130                 135                 140

Ser Asp Arg Met Val Phe Val Arg Ala Val His Glu Ala Asn Trp Met
145                 150                 155                 160

Asn Glu Met Glu Ile Ser Ile Tyr Asp Ser Trp Phe Asp Pro Val Val
                165                 170                 175

Ser Thr Leu Pro Gly Leu Ile Pro Asp Gly Phe Ile Tyr Leu Arg Ala
            180                 185                 190

Ser Pro Asp Thr Cys His Lys Arg Met Met Leu Arg Lys Arg Thr Glu
        195                 200                 205

Glu Gly Gly Val Ser Leu Glu Tyr Leu Arg Gly Leu His Glu Lys His
    210                 215                 220

Glu Ser Trp Leu Phe Pro Phe Glu Ser Gly Asn His Gly Val Leu Ser
225                 230                 235                 240

Val Ser Glu Leu Pro Leu Asn Phe Asp Lys Phe Cys Val Pro Pro Glu
                245                 250                 255

Ile Arg Asp Arg Val Phe Tyr Leu Glu Gly Asn His Met His Pro Ser
            260                 265                 270

Ile Gln Lys Val Pro Ala Leu Val Leu Asp Cys Glu Pro Asn Ile Asp
        275                 280                 285

Phe Asn Arg Asp Ile Glu Ala Lys Arg Gln Tyr Ala Arg Gln Val Ala
    290                 295                 300

Asp Phe Phe Glu Phe Val Lys Lys Gln Glu Val Met Pro Gly Ala
305                 310                 315                 320

Gly Glu Glu Gln Pro Lys Gly Asn Gln Ala Pro Val Met Leu Pro Gln
                325                 330                 335

Asn Gly Gly Leu Trp Val Pro Gly Gly Lys Phe Ser Glu Ser Thr Leu
            340                 345                 350

Asn Leu Asp Phe Arg Arg Asn Met Ser Phe Met Ser His
        355                 360                 365
```

```
<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

Tyr Ile Gly Ser Arg
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Ile Lys Val Ala Val
1               5

<210> SEQ ID NO 20
<211> LENGTH: 37
<212> TYPE: DNA
<213> ORGANISM: Artificial Sequence
<220> FEATURE:
<223> OTHER INFORMATION: Synthetic Construct

<400> SEQUENCE: 20
agcttctcga ggtcgacgga tccgcatgcc aattgat                              37

<210> SEQ ID NO 21
<211> LENGTH: 35
<212> TYPE: DNA
<213> ORGANISM: Artificial Sequence
<220> FEATURE:
<223> OTHER INFORMATION: Synthetic Construct

<400> SEQUENCE: 21
cgatcaattg gcatgcggat ccgtcgacct cgaga                                35
```